(12) United States Patent
Ohgiya et al.

(10) Patent No.: US 8,906,895 B2
(45) Date of Patent: Dec. 9, 2014

(54) OPTICALLY ACTIVE DIBENZYLAMINE DERIVATIVE, AND METHOD FOR PREPARING THEREOF

(75) Inventors: Tadaaki Ohgiya, Saitama (JP); Takeshi Murakami, Tokyo (JP); Katsutoshi Miyosawa, Tokyo (JP); Kimiyuki Shibuya, Saitama (JP); Koichi Yamazaki, Tokyo (JP); Taichi Kusakabe, Chiba (JP)

(73) Assignee: Kowa Company, Ltd., Aichi (JP)

( * ) Notice: Subject to any disclaimer, the term of this patent is extended or adjusted under 35 U.S.C. 154(b) by 0 days.

(21) Appl. No.: 13/700,849

(22) PCT Filed: Jun. 3, 2011

(86) PCT No.: PCT/JP2011/062751
§ 371 (c)(1),
(2), (4) Date: Mar. 13, 2013

(87) PCT Pub. No.: WO2011/152508
PCT Pub. Date: Dec. 8, 2011

(65) Prior Publication Data
US 2013/0225814 A1    Aug. 29, 2013

(30) Foreign Application Priority Data

Jun. 4, 2010  (JP) .................. 2010-128585
Sep. 29, 2010  (JP) .................. 2010-218299

(51) Int. Cl.
*A61K 31/495* (2006.01)
*C07D 239/48* (2006.01)
*C07D 239/47* (2006.01)

(52) U.S. Cl.
CPC .................. *C07D 239/47* (2013.01)
USPC .................. 514/183; 544/298

(58) Field of Classification Search
CPC .................. C07D 239/47
See application file for complete search history.

(56) References Cited

U.S. PATENT DOCUMENTS

| 5,189,208 | A | 2/1993 | Stahly | |
| 7,659,271 | B2 * | 2/2010 | Ohgiya et al. | ............. 514/235.8 |

FOREIGN PATENT DOCUMENTS

| CN | 101679309 A | 3/2010 |
| JP | 6-509096 | 10/1994 |
| TW | 2009/06804 | 2/2009 |
| WO | 2008/129951 | 10/2008 |
| WO | 2009/143633 | 12/2009 |
| WO | 2012/046681 | 4/2012 |

OTHER PUBLICATIONS

New Zealand Office action, mail date is Jul. 18, 2013.
U.S. Appl. No. 13/824,782 (U.S. national stage application of PCT/JP2011/07242, which was published as WO 2012/-46681), Apr. 12, 2012.
Hirayama et al., Yuki Kogobutsu Kessho Sakusei Handbook, Maruzen Co., Ltd., 2008, pp. 129-136 and English language translation.
Office Action issued with respect to Eurasian Patent Application No. 201291447, mail date is Oct. 15, 2013.
Extended European Search Report issued with respect to European Application No. 11789909.6, mail date is Nov. 5, 2013.
Chinese Office Action in regards to Chinese Application No. 201180027596.9, dated Feb. 8, 2014, with English Translation.
Hirayama et al., Yuki Kogobutsu Kessho Sakusei Handbook, Maruzen Co., Ltd., 2008, pp. 130-135.
Nippon Rinsho, vol. 59, Extra issue 3, Hyperlipidemia (vol. 2), 2001, pp. 381-386.
Abifadel et al., "Mutations in PCSK9 cause autosomal dominant hyper cholesterolemia", Nature Genetics, vol. 34, No. 2, 2003, pp. 154-156.
Cohen et al., "Sequence Variations in PCSK9, Low LDL, and Protection against Coronary Heart Disease", N. Engl. J. Med., 354, 2006, pp. 1264-1272.
Rashid et al., "Decreased plasma cholesterol and hypersensitivity to statins in mice lacking Pcsk9", Proc. Natl. Acad. Sci. USA, vol. 102, 2005, pp. 5374-5379.
Chan et al., "A proprotein convertase subtilisin/kexin type 9 neutralizing antibody reduces serum cholesterol in mice and nonhuman primates", Proc. Natl. Acad. Sci. USA, vol. 106, No. 24, 2009, pp. 9820-9825.
Graham et al., "Antisense inhibition of proprotein convertase sutilisin/kexin type 9 reduces serum LDL in hyperlipidemic mice", J. Lipid Res., vol. 48, 2007, pp. 763-767.
Frank-Kamenetsky et al., "Therapeutic RNAi targeting PCSK9 acutely lowers plasma cholesterol in rodents and LDL cholesterol in nonhuman primates", Proc. Natl. Acad. Sci. USA, vol. 105, No. 33, 2008, pp. 11915-11920.
Cameron et al., "Berberine decreases PCSK9 expression in HepG2 cells", Atherosclerosis, vol. 201, No. 2, 2008, pp. 266-273.
Bassi et al., "Proprotein Convertases: "Master Switches" in the Regulation of Tumor Growth and Progression", Molecular Carcinogenesis, vol. 44(3), (2005), pp. 151-161.
Chretien, "Endoproteolysis in health and diseases—implications of proprotein convertases (PCs)", J. Mol. Med., 83, 2005, pp. 842-843.
Basak, "Inhibitors of proprotein convertases", J. Mol. Med., 83, 2005, pp. 844-855.

(Continued)

*Primary Examiner* — Noble Jarrell
*Assistant Examiner* — John S Kenyon
(74) *Attorney, Agent, or Firm* — Greenblum & Bernstein, P.L.C.

(57) ABSTRACT

Substantially optically pure (S)-trans-{4-[({2-[({1-[3,5-bis (trifluoromethyl)phenyl]ethyl}{5-[2-(methylsulfonyl) ethoxy]pyrimidin-2-yl}amino)methyl]-4-(trifluoromethyl) phenyl}(ethyl)amino)methyl]cyclohexyl}acetic acid, or a salt thereof, or a solvate thereof, which has actions of reducing amount of PCSK9 protein and increasing amount of LDL receptor.

12 Claims, No Drawings

(56) References Cited

OTHER PUBLICATIONS

Kourimate et al., "Dual Mechanisms for the Fibrate-mediated Repression of Proprotein Convertase Subtilisin/Kexin Type 9", J. Biol. Chem., vol. 283, No. 15, 2008, pp. 9666-9673.

Usui et al., "A new on-line dual enzymatic method for simultaneous quantification of cholesterol and triglycerides in lipoproteins by HPLC", J. Lipid. Res., vol. 43, 2002, pp. 805-814.

Search report from PCT/JP2011/062751, Jun. 22, 2011.

International Preliminary Report on Patentability and Written Opinion of the Searching Authority for PCT/JP2011/062751, Jan. 17, 2013.

Steinberg et al., "Inhibition of PCSK9: A powerful weapon for achieving ideal LDL cholesterol levels", PNAS, vol. 106, No. 24, Jun. 16, 2009, pp. 9546-9547.

Australian Office Action in regards to Australian Patent Application No. 2011259929, dated Dec. 4, 2013.

Japanese Office Action in regards to Japanese Application No. 2012-518458, dated Jan. 31, 2014, with partial English Translation.

Eurasian Office Action in respect to Eurasian Application No. 201291447, dated Jun. 10, 2014 with English Translation.

Taiwanese Office Action with English Translation in respect to Taiwanese Application No. 100119614, dated Aug. 20, 2014.

Mexican Office Action with partial English in respect to Mexican Application No. MX/a/2012/014149, dated Sep. 9, 2014.

Chinese Office Action with English Translation in respect Chinese Application No. 201180027596.9, dated Sep. 10, 2014.

* cited by examiner

OPTICALLY ACTIVE DIBENZYLAMINE DERIVATIVE, AND METHOD FOR PREPARING THEREOF

SEQUENCE LISTING

The instant application contains a Sequence Listing which has been submitted in ASCII Format via EFS-Web and is hereby incorporated by reference in its entirety. Said ASCII copy, Created on Jan. 4, 2013, is named P42944.txt and is 973 bytes in size.

TECHNICAL FIELD

The present invention relates to an optically active dibenzylamine derivative useful as an active ingredient of medicament or the like, and a method for preparing the same.

BACKGROUND ART

In recent years, patients suffering from dyslipidemia (hyperlipidemia) and arteriosclerotic diseases induced thereby have been rapidly increased due to changes in dietary habits to take high calorie and high cholesterol-type foods with improvement of a living standard, obesity, lack of exercise, aging, and the like. It has been revealed from many etiological researches including the Framingham study that a low-density lipoprotein (LDL) cholesterol level positively correlates to an onset rate of heart diseases. Therefore, in drug therapies for dyslipidemia and arteriosclerosis, reduction of a LDL cholesterol value has been importantly focused (Non-patent document 1).

For hyper-LDL cholesterolemia, which is one of potent risk factors of cardiovascular diseases, therapeutic methods have been markedly progressed by the launch of HMG-CoA reductase inhibitors (statins). However, although statins potently reduce LDL cholesterol, decrease in cardiac accidents and mortality of cardiovascular diseases remains as high as about 30%. It is considered that a lower death risk of cardiovascular diseases can be achieved by further reducing LDL cholesterol. However, a high dose administration of statins cannot be applied due to enhanced increased risk of rhabdomyolysis.

Therefore, a medicament has been desired which has a potent reducing action on blood LDL cholesterol and is based on different mode of action from that of statins.

Proprotein convertases (PCs) are members of the mammalian serine protease family, of which homology to subtilisin in bacteria and kexin in yeast has been observed. One of PCs, PCSK9 (proprotein convertase subtilisin/kexin 9), is mainly expressed in the liver and secreted extracellularly, and then bound with LDL receptor on the membrane surfaces of hepatocytes to promote migration of the LDL receptor into the cells. The LDL receptor migrated into the cells are decomposed by cell organelles. Since the LDL receptor has a function of transporting lipoproteins containing LDL cholesterol to the liver from circulating blood, production of the PCSK9 protein inhibits uptake of blood LDL cholesterol into the liver, which results in an increase of blood LDL cholesterol level. In fact, it is known that LDL blood cholesterol level is high in humans with a function acquisition-type mutation in the PCSK9 gene, which relates to autosomal dominant hypercholesterolemia (Non-patent document 2). Whilst, a low level of blood LDL cholesterol is maintained in humans with a function deletion type mutation in the PCSK9 gene (Non-patent document 3). Further, it has been demonstrated in an animal that LDL cholesterol level is low in mice deficient in the PCSK9 gene of the liver (Non-patent document 4).

It is considered from the reasons set forth above that reduction of the amount of the PCSK9 protein by suppression of the production thereof or inhibition against the function of the PCSK9 protein leads to increase in the amount of the LDL receptor, and thus provides a potent LDL cholesterol-reducing action.

Under the circumstances, active researches have recently been conducted on functional inhibition of the PCSK9 protein or suppression of the production thereof. For example, as those using an antibody or antisense oligonucleotide, functional inhibition of the PCSK9 protein using a monoclonal antibody directed to PCSK9, suppression of the PCSK9 protein production based on RNA interference, and the like have been reported (Non-patent documents 5 to 7). Further, as those using a low molecular weight compound, it has been reported that berberine reduces mRNA and protein level of PCSK9 in HepG2 cells (Non-patent document 8), and 5-azacytidine, which is an annexin A2 activator, promotes binding of the PCSK9 protein with annexin A2 and suppresses decomposition of LDL receptor (Patent document 1). However, almost no compounds with a low molecular weigh as inhibitors against PCSK9 protein function or suppressors against PCSK9 protein production have been reported except for those mentioned above.

Patent document 2 discloses pyrimidine compounds having a dibenzylamine structure, which have potent inhibitory activity against cholesteryl ester transfer protein (CETP), and also have a potent blood HDL cholesterol-increasing action. The document discloses the compound of the following formula (I) as a racemate in Example 45:

[Formula 1]

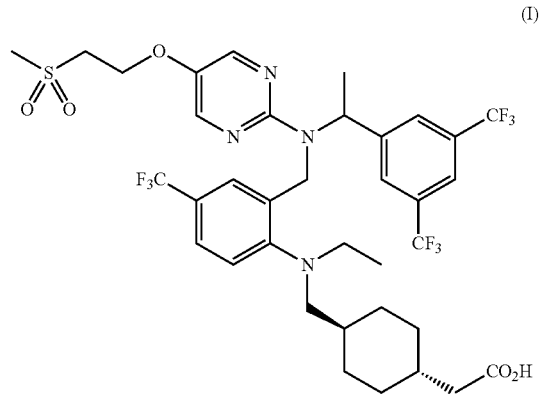 [SMILES: CCN(C[C@H]1CC[C@H](CC(=O)O)CC1)c1ccc(C(F)(F)F)cc1CN(c1ncc(OCCSC)cn1)C(C)c1cc(C(F)(F)F)cc(C(F)(F)F)c1]

(I)

(trans-{4-[({2-[({1-[3,5-bis(trifluoromethyl)phenyl] ethyl}{5-[2-(methylsulfonyl)ethoxy]pyrimidin-2-yl}amino) methyl]-4-(trifluoromethyl)phenyl}(ethyl)amino)methyl] cyclohexyl}acetic acid, henceforth also referred to as "racemate compound (I)" in the specification). However, any relationship between the racemate compound (I) and the PCSK9 protein has not been described or suggested.

Since PCs have influences on proliferation, motility, adhesion, and invasion of cancer cells, they have been focused as a target of cancer treatment (Non-patent document 9). There are also known relationship of PCs with obesity, diabetes, and Alzheimer disease, and involvements of PCs in diseases such as viral infectious diseases including acquired immunodeficiency syndrome (AIDS) and severe acute respiratory syndrome (SARS) (Non-patent documents 10 and 11).

Therefore, use of a compound having a reducing action on amount of PCSK9 protein or an inhibitory action against PCSK9 protein function as an active ingredient of a medicament for the aforementioned diseases is also expected.

PRIOR ART REFERENCES

Patent Documents

Patent document 1: International Patent Publication WO2009/143633
Patent document 2: International Patent Publication WO2008/129951

Non-patent Documents

Non-patent document 1: Nippon Rinsho, Vol. 59, Extra issue 3, Hyperlipidemia (vol. 2), 381-386 (2001)
Non-patent document 2: Nat. Genet., 34, 154-156 (2003)
Non-patent document 3: N. Engl. J. Med., 354, 1264-1272 (2006)
Non-patent document 4: Proc. Natl. Acad. Sci. USA, 102, 5374-5379 (2005)
Non-patent document 5: Proc. Natl. Acad. Sci. USA, 106, 9820.9825 (2009)
Non-patent document 6: J. Lipid Res., 48, 763.767 (2007)
Non-patent document 7: Proc. Natl. Acad. Sci. USA, 105, 11915-11920 (2008)
Non-patent document 8: Atherosclerosis, 201 (2), 266.73 (2008)
Non-patent document 9: Mol. Carcinogen., 44 (3), 151-161 (2005)
Non-patent document 10: J. Mol. Med., 83, 842.843 (2005)
Non-patent document 11: J. Mol. Med., 83, 844-855 (2005)

SUMMARY OF THE INVENTION

Object to be Achieved by the Invention

An object of the present invention is to provide a low molecular weight compound having actions of reducing amount of the PCSK9 protein and increasing amount of LDL receptor, and a medicament comprising said low molecular weight compound as an active ingredient.

Means for Achieving the Object

The inventors of the present invention conducted various researches to achieve the aforementioned object. As a result, they found that the racemate compound (I) and one of enantiomers thereof, (R)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid represented by the following formula (II) (henceforth also referred to as "(R)-isomer compound (II)" in the specification):

[Formula 2]

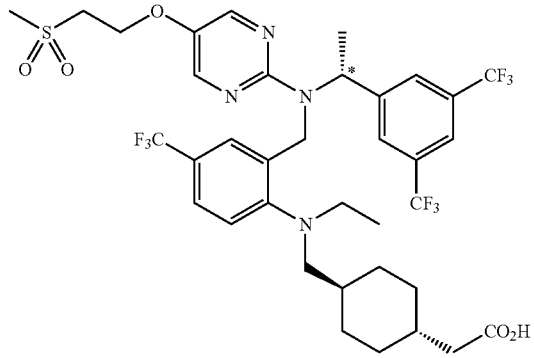

(II)

had almost no actions of reducing amount of the PCSK9 protein and increasing amount of LDL receptor, whilst they also found that levorotatory (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}ethyl)amino)methyl]cyclohexyl}acetic acid represented by the following formula (III) (henceforth also referred to as "(S)-isomer compound (III)" in the specification):

[Formula 3]

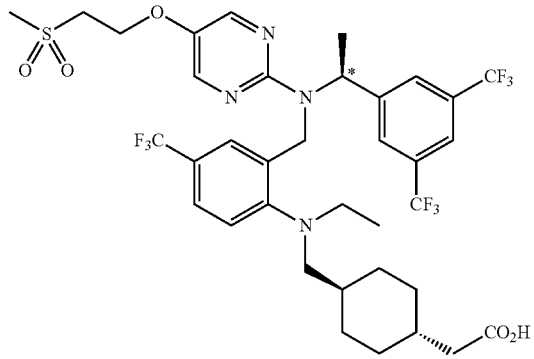

(III)

or a salt thereof, or a solvate thereof had actions of potently reducing the amount of the PCSK9 protein and increasing the amount of LDL receptor. The present invention was achieved on the basis of the above findings.

The present invention thus provides (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid, or a salt thereof, or a solvate thereof (preferably, substantially optically pure (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid, or a salt thereof, or a solvate thereof).

As another aspect, the present invention provides a levorotatory enantiomer of trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid, or a salt thereof, or a solvate thereof (preferably, a substantially optically pure levorotatory enantiomer of trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid, or a salt thereof, or a solvate thereof).

The present invention also provides a medicament comprising the (S)-isomer compound (III), or a salt thereof, or a solvate thereof as an active ingredient.

The present invention also provides a pharmaceutical composition containing the (S)-isomer compound (III), or a salt thereof, or a solvate thereof as an active ingredient, and a pharmaceutically acceptable carrier.

The medicament and the pharmaceutical composition reduce blood LDL cholesterol, and therefore they can be used as a medicament for prophylactic and/or therapeutic treatment of a disease resulting from a high blood LDL cholesterol state (for example, hyper-LDL cholesterolemia, dyslipidemia (hyperlipidemia), arteriosclerosis, atherosclerosis, peripheral vascular diseases, hypercholesterolemia, familial hypercholesterolemia, cardiovascular functional disorders, angina pectoris, ischemia, cardiac ischemia, thrombosis, myocardial infarction, reperfusion disorders, angioplasty restenosis, hypertension, and the like).

The present invention further provides use of the (S)-isomer compound (III), or a salt thereof, or a solvate thereof for manufacture of a medicament for prophylactic and/or therapeutic treatment of a disease resulting from a high blood LDL cholesterol state; and the (S)-isomer compound (III), or a salt thereof, or a solvate thereof for use in prophylactic and/or therapeutic treatment of a disease resulting from a high blood LDL cholesterol state.

The present invention also provides a PCSK9 mRNA expression-suppressing agent comprising the (S)-isomer compound (III), or a salt thereof, or a solvate thereof as an active ingredient; a PCSK9 protein amount-reducing agent comprising the (S)-isomer compound (III), or a salt thereof, or a solvate thereof as an active ingredient; a PCSK9 protein production-suppressing agent comprising the (S)-isomer compound (III), or a salt thereof, or a solvate thereof as an active ingredient; and an LDL receptor amount-increasing agent comprising the (S)-isomer compound (III), or a salt thereof, or a solvate thereof as an active ingredient.

The present invention further provides use of the (S)-isomer compound (III), or a salt thereof, or a solvate thereof for manufacture of a PCSK9 mRNA expression-suppressing agent, a PCSK9 protein amount-reducing agent, a PCSK9 protein production-suppressing agent, or an LDL receptor amount-increasing agent; and the (S)-isomer compound (III), or a salt thereof, or a solvate thereof for use as an active ingredient of a PCSK9 mRNA expression-suppressing agent, a PCSK9 protein amount-reducing agent, a PCSK9 protein production-suppressing agent, or an LDL receptor amount-increasing agent.

The present invention also provides a medicament for prophylactic and/or therapeutic treatment of disease in which PCs are involved (cancer, obesity diabetes, Alzheimer disease, viral infectious diseases, and the like) comprising the (S)-isomer compound (III), or a salt thereof, or a solvate thereof as an active ingredient.

The present invention further provides use of the (S)-isomer compound (III), or a salt thereof, or a solvate thereof for manufacture of a medicament for prophylactic and/or therapeutic treatment of a disease in which PCs are involved; and the (S)-isomer compound (III), or a salt thereof, or a solvate thereof for use in prophylactic and/or therapeutic treatment of a disease in which PCs are involved.

As still other aspects, the present invention provides an HMG-CoA reductase mRNA expression-suppressing agent comprising the racemate compound (I), the compound described in Patent document 2, Example 44 (trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid), or an enantiomer thereof, or a salt thereof, or a solvate thereof as an active ingredient; an HMG-CoA reductase production-suppressing agent comprising the racemate compound (I), the compound described in Patent document 2, Example 44, or an enantiomer thereof, or a salt thereof, or a solvate thereof as an active ingredient; and a medicament for prophylactic and/or therapeutic treatment of a disease resulting from expression of HMG-CoA reductase mRNA (for example, inflammation, cancer, Alzheimer disease, osteoporosis, prostatic hypertrophy, glomerular diseases, vermination, virus infection, psoriasis, macular degeneration, and the like) containing the racemate compound (I), the compound described in Patent document 2, Example 44, or an enantiomer thereof, or a salt thereof, or a solvate thereof as an active ingredient.

The present invention also provides use of the racemate compound (I), the compound described in Patent document 2, Example 44, or an enantiomer thereof, or a salt thereof, or a solvate thereof for manufacture of an HMG-CoA reductase mRNA expression-suppressing agent, an HMG-CoA reductase production-suppressing agent, or a medicament for prophylactic and/or therapeutic treatment of a disease resulting from expression of HMG-CoA reductase mRNA; and the racemate compound (I), the compound described in Patent document 2, Example 44, or an enantiomer thereof, or a salt thereof, or a solvate thereof for use as an active ingredient of an HMG-CoA reductase mRNA expression-suppressing agent, an HMG-CoA reductase production-suppressing agent, or a medicament for prophylactic and/or therapeutic treatment of a disease resulting from expression of HMG-CoA reductase mRNA.

The present invention also provides a method for suppressing expression of PCSK9 mRNA in a mammal including human in vivo, which comprises the step of administrating an effective amount of the (S)-isomer compound (III), or a salt thereof, or a solvate thereof to the mammal including human; a method for reducing amount of PCSK9 protein in a mammal including human in vivo, which comprises the step of administrating an effective amount of the (S)-isomer compound (III), or a salt thereof, or a solvate thereof to the mammal including human; a method for suppressing PCSK9 protein production in a mammal including human in vivo, which comprises the step of administrating an effective amount of the (S)-isomer compound (III), or a salt thereof, or a solvate thereof to the mammal including human; a method for increasing amount of LDL receptor in a mammal including human in vivo, which comprises the step of administrating an effective amount of the (S)-isomer compound (III), or a salt thereof, or a solvate thereof to the mammal including human; and a method for reducing blood LDL in a mammal including human in vivo, which comprises the step of administrating an effective amount of the (S)-isomer compound (III), or a salt thereof, or a solvate thereof to the mammal including human.

The present invention also provides a method for prophylactic and/or therapeutic treatment of a disease resulting from a high blood LDL cholesterol state in a mammal including human, which comprises the step of administrating an effective amount of the (S)-isomer compound (III), or a salt thereof, or a solvate thereof to the mammal including human.

The present invention further provides a method for prophylactic and/or therapeutic treatment of a disease in which PCs are involved in a mammal including human, which comprises the step of administrating an effective amount of the (S)-isomer compound (III), or a salt thereof, or a solvate thereof to the mammal including human.

The present invention further provides a method for suppressing expression of HMG-CoA reductase mRNA in a mammal including human in vivo, which comprises the step of administrating an effective amount of the racemate compound (I), the compound described in Patent document 2, Example 44, or an enantiomer thereof, or a salt thereof, or a solvate thereof to the mammal including human; a method for suppressing production of HMG-CoA reductase in a mammal including human in vivo, which comprises the step of administrating an effective amount of the racemate compound (I), the compound described in Patent document 2, Example 44, or an enantiomer thereof, or a salt thereof, or a solvate thereof to the mammal including human; and a method for prophylactic and/or therapeutic treatment of a disease resulting from expression of HMG-CoA reductase mRNA, which comprises the step of administrating an effective amount of the racemate compound (I), the compound described in Patent document 2, Example 44, or an enantiomer thereof, or a salt thereof, or a solvate thereof to the mammal including human.

The present invention also provides a method for preparing the (S)-isomer compound (III) and/or the (R)-isomer compound (II) in a substantially optically pure form.

Although Patent document 2 describes a method for preparing the racemate compound (I), it has been extremely difficult to prepare the (S)-isomer compound (III) or the (R)-isomer compound (II) in a substantially optically pure form as described below.

Specifically, as a general point of view, it is known that a substantially optically pure compound may be prepared by synthesizing racemate, and then subjecting the racemate to optical resolution using a chiral column.

However, in the optical resolution using a chiral column, it may sometimes be very difficult to set conditions of the resolution for a certain type of compound, and the process is unsuitable for industrial scale production. Practically, it was found that the set of the conditions of the optical resolution using a chiral column for preparing substantially optically pure (S)-isomer compound (III) or (R)-isomer compound (II) was extremely difficult. More specifically, it was attempted to fractionate each enantiomer from the racemate compound (I) prepared in accordance with the method described in Patent document 2, Example 45 while variously changing the conditions such as types of a chiral column (for example, CHIRALCEL OD-H, CHIRALCEL OJ-H, and the like), types of a solvent used as a mobile phase (for example, MeOH/TFA mixture, EtOH/TFA mixture, and the like), and flow rate of the mobile phase. However, the resolution was not successful under almost all conditions applied. Under the circumstances, it was found that each enantiomer was successfully separated under the conditions described in Example 1-1 which will be mentioned later. However, it was also found that a decomposition product (ethyl ester compound) was produced under the aforementioned conditions.

Patent document 2 also discloses that the racemate compound (I) can be prepared by a method comprising the steps of coupling an intermediate compound (a) and a racemate benzyl bromide compound (b) in the presence of a base, hydrolyzing the ester group of the resulting compound (c) to prepare a compound (d), and finally oxidizing the sulfur atom of the compound (d) according to Scheme 1 shown below.

Scheme 1

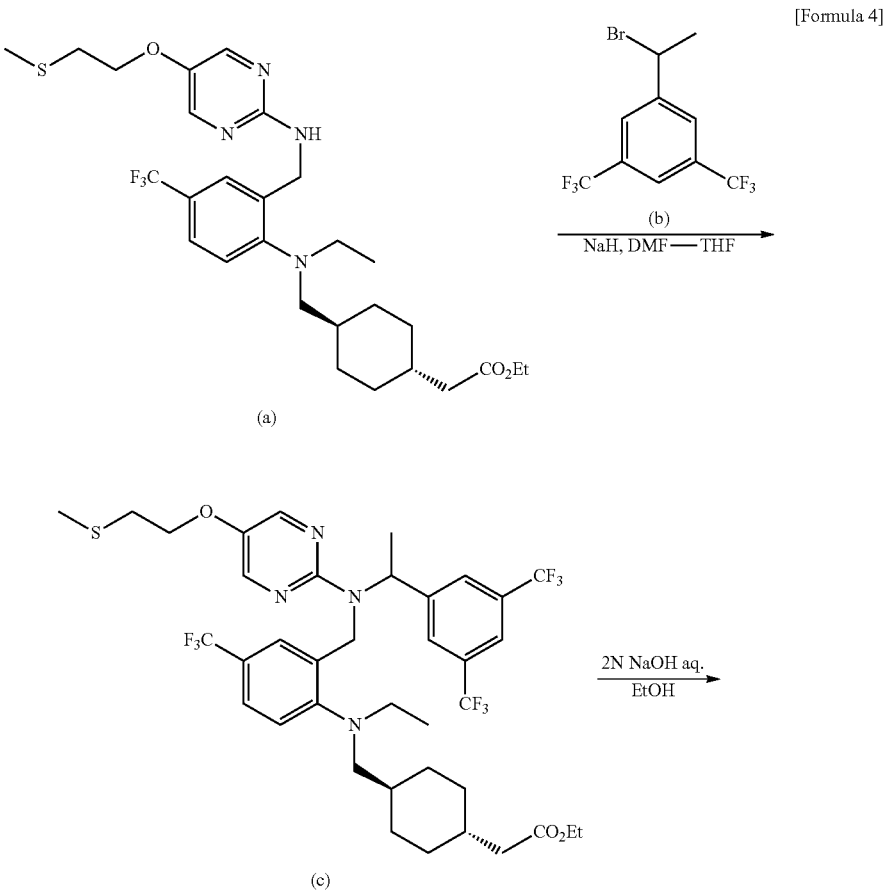

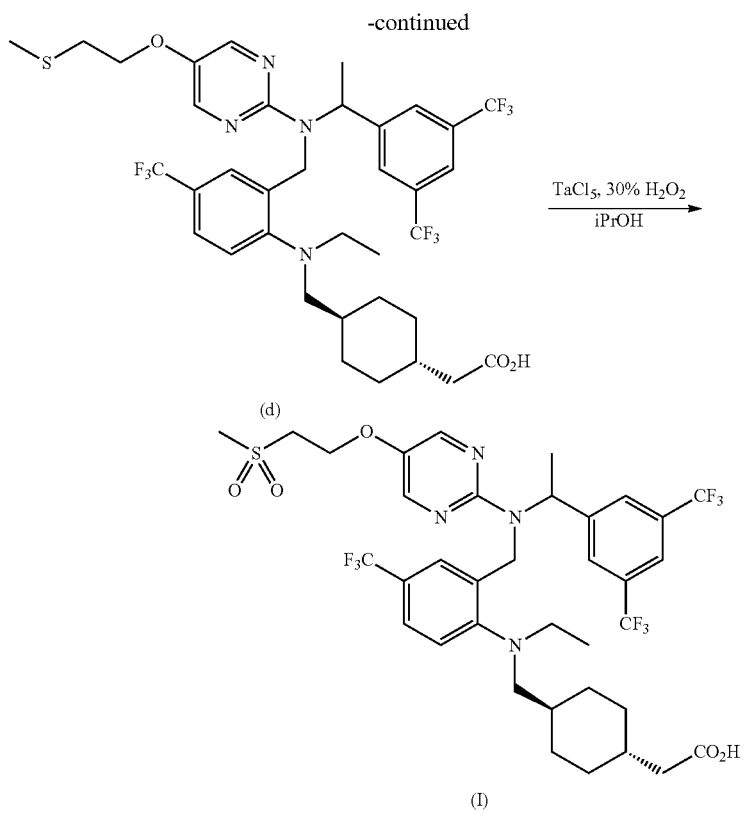

With reference to Scheme 1, the inventors of the present invention attempted to obtain substantially optically pure (S)-isomer compound (III) or the (R)-isomer compound (II) by using optically active 1-[3,5-bis(trifluoromethyl)phenyl]-1-methanesulfonyloxyethane instead of the racemate benzyl bromide compound (b). However, the elimination reaction of 1-[3,5-bis(trifluoromethyl)phenyl]-1-methanesulfonyloxyethane preferentially occurred, and the objective compound was not successfully obtained.

Further, the preparation was further attempted by using an optically active benzylating agent having a leaving group such as toluenesulfonyl group, chloromethanesulfonyl group, or 2,4,6-triisopropylbenzenesulfonyl group instead of methanesulfonyl group. However, substantially optically pure (S)-isomer compound (III) or the (R)-isomer compound (II) was not successfully obtained as in the case of using 1-[3,5-bis(trifluoromethyl)phenyl]-1-methanesulfonyloxyethane.

When the benzyl bromide compound (b) was used, introduction of [3,5-bis(trifluoromethyl)phenyl]-1-ethyl group into the nitrogen atom of the intermediate compound (a) was already successfully achieved. Accordingly, it can be contemplated to obtain substantially optically pure (S)-isomer compound (III) or (R)-isomer compound (II) by using an optically active benzyl bromide compound instead of racemate benzyl bromide compound (b).

However, it is generally known that, in a nucleophilic substitution reaction in which bromide ion is eliminated, the bromide ion produced by the reaction reacts with benzyl bromide in the reaction system, and racemization advances. Further, it is also generally known that, in a nucleophilic substitution reaction at benzyl position, an SN1 type substitution reaction also competitively occurs due to stabilization of the benzyl cation, and therefore racemization partially occurs.

As for the compound having a moderate optical purity obtained as a result of decrease in optical purity due to partial racemization (in the specification, "compound having a moderate optical purity" means a compound having an optical purity not lower than about 10% ee and lower than about 90% ee, preferably about 20 to 80% ee, and most preferably about 40 to 70% ee, and the compound having the moderate optical purity may also be henceforth referred to as "semi-chiral compound". Further, as for the semi-chiral compound, when a compound, in which the asymmetric carbon atom indicated with * in the partial structure shown below is in the S-configuration, is present in a larger amount as compared with a compound in the R-configuration, the compound is specifically referred to as "(S)-isomer-dominant semi-chiral compound". Whilst, as for the semi-chiral compound, when the compound in which the asymmetric carbon atom indicated with * is in the R-configuration is present in a larger amount as compared with the compound in the S-configuration, the compound is specifically referred to as "(R)-isomer-dominant semi-chiral compound".)

[Formula 5]

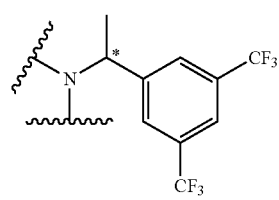

it is known that optical purity thereof can be increased by preferentially crystallizing one of the enantiomers.

However, according to the study of the inventors of the present invention, crystallization did not advance in the case of the racemate compound (I) or an ethyl ester derivative thereof, and optical purity thereof was not successfully increased by the preferential crystallization.

Under the circumstances as described above, the inventors of the present invention converted the carboxylic acid of the racemate compound (I) into benzyl ester, and found that the resulting benzyl ester compound was successfully isolated as a crystal comprising the racemate as a main component.

Then, by preparing a semi-chiral compound (IV) of an arylalkyl or heteroarylalkyl ester compound, and then crystallizing crystals of a low optical purity dominantly containing the racemate as a component (henceforth also referred to as "racemate-dominant crystals") and removing the crystals to obtain an arylalkyl or heteroarylalkyl ester compound (V) or (V') with a high optical purity, and then by using the compound (V) or (V') as a starting material as shown in Scheme 2 mentioned below, the inventors successfully prepared a desired enantiomer of the racemate compound (I) ((S)-isomer compound (III) or (R)-isomer compound (II)) in a substantially optically pure form.

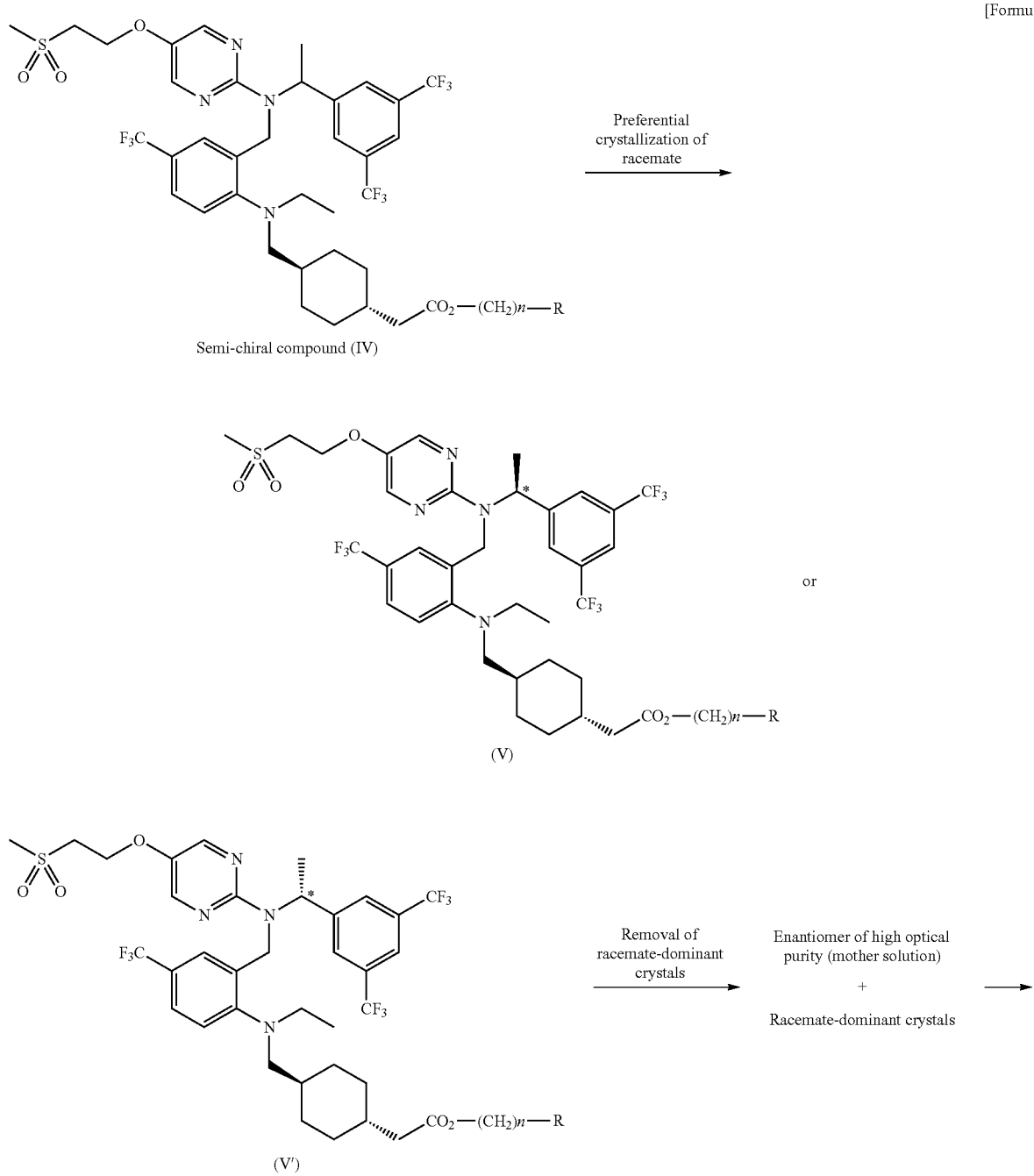

Scheme 2

[Formula 6]

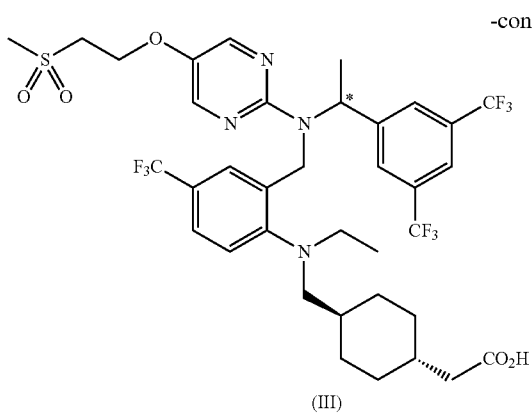

(III)

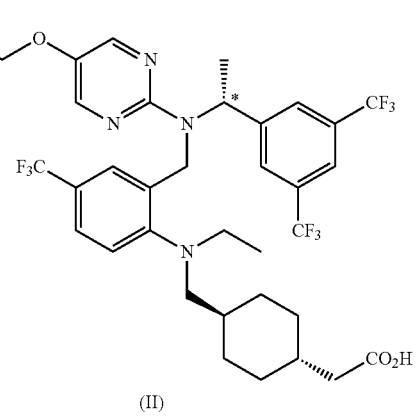

(II)

(In the scheme, R represents a $C_{6-10}$ aryl group which may have a substituent, or a 5- to 10-membered heteroaryl group which may have a substituent, and n represents an integer of 1 to 6.)

The present invention thus provides a method for preparing substantially optically pure (S)-isomer compound (III) or substantially optically pure (R)-isomer compound (II), or a salt thereof, or a solvate thereof, which comprises the step of removing racemate-dominant crystals from a semi-chiral compound of a compound represented by the following general formula (IV):

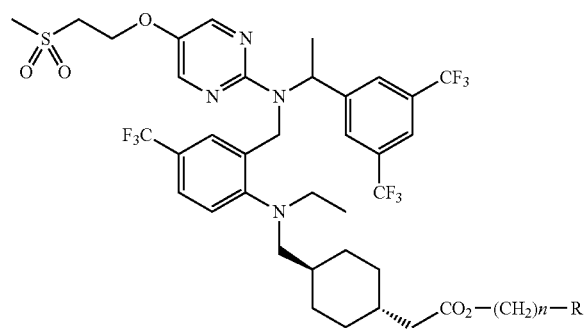

(IV)

(in the formula, R represents a $C_{6-10}$ aryl group which may have a substituent, or a 5- to 10-membered heteroaryl group which may have a substituent, and n represents an integer of 1 to 6) by preferential crystallization in a solvent to obtain a substantially optically pure compound represented by the following general formula (V) or (VI):

[Formula 8]

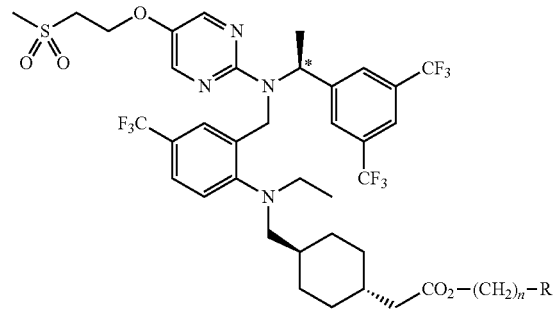

(V)

or

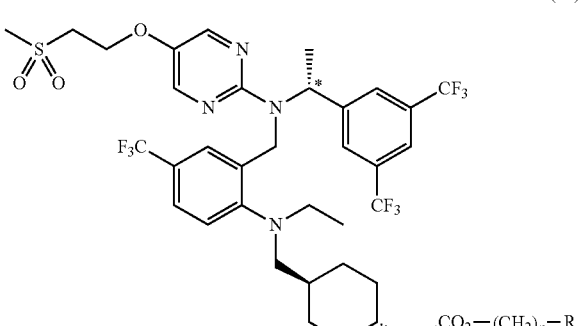

(V')

(in the formulas, R and n have the same meanings as those defined for the general formula (IV)).

By the aforementioned method, when the compound represented by the general formula (IV) is an (S)-isomer-dominant semi-chiral compound, the (S)-isomer compound (III) can be prepared, and when the compound represented by the general formula (IV) is an (R)-isomer-dominant semi-chiral compound, the (R)-isomer compound (II) can be prepared.

The present invention further provides the aforementioned method, which further comprises the step of removing the group represented as —$(CH_2)_n$—R from the compound represented by the general formula (V) or (V').

The present invention further provides:
(A) the aforementioned method, which further comprises the step of reacting a semi-chiral compound of a compound represented by the following general formula (VI):

[Formula 9]

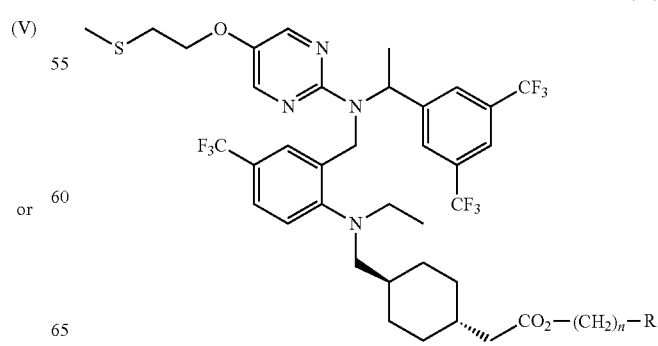

(VI)

(in the formula, R and n have the same meanings as those defined for the general formula (IV)) with an oxidizing agent in a solvent to prepare a semi-chiral compound of a compound represented by the general formula (IV);

(B) the aforementioned method (A), which further comprises the step of reacting a semi-chiral compound of a compound represented by the following formula (VII):

[Formula 10]

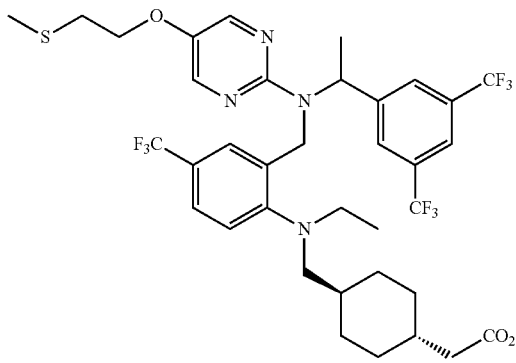

(VII)

with a compound represented by the following general formula (VIII)

[Formula 11]

R—(CH$_2$)$_n$—OH    (VIII)

(in the formula, R and n have the same meanings as those defined for the general formula (IV)) in a solvent in the presence of a catalyst to prepare the semi-chiral compound of a compound represented by the general formula (VI);

(C) the aforementioned method (B), which further comprises the step of hydrolyzing a semi-chiral compound of a compound represented by the following general formula (IX):

[Formula 12]

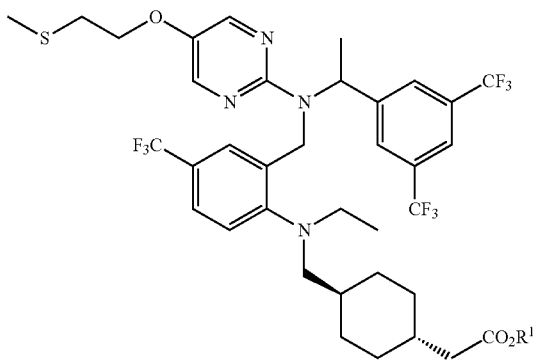

(IX)

(in the formula, R$^1$ represents a C$_{1-6}$ alkyl group) in a solvent in the presence of a base to prepare the semi-chiral compound of a compound represented by the formula (VII); and (D) the aforementioned method (C), which further comprises the step of reacting a compound represented by the following general formula (X) or (X'):

[Formula 13]

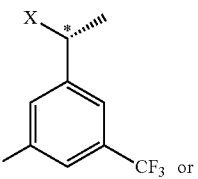

(X)

or

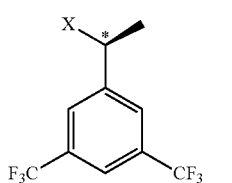

(X')

(in the formula, X represents a halogen atom), and a compound represented by the following general formula (XI):

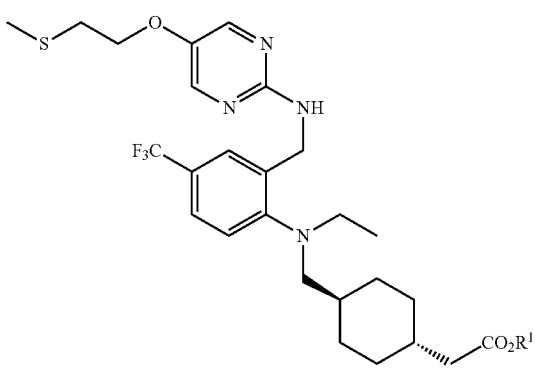

(XI)

(in the formula, R$^1$ has the same meaning as that defined for the general formula (IX)) in a solvent in the presence of a base to prepare the semi-chiral compound of a compound represented by the general formula (IX).

The present invention also provides the aforementioned method (D), which further comprises the step of halogenating optically active 1-[3,5-bis(trifluoromethyl)phenyl]ethanol in the presence of a halogenating agent to prepare the compound represented by the general formula (X) or (X').

As another aspect, the present invention provides a compound represented by the aforementioned general formula (IV), or a salt thereof, or a solvate thereof. The compound wherein R is phenyl, and n is 1, a salt thereof, or a solvate thereof is a preferred embodiment of this invention.

The present invention further provides a substantially optically pure compound represented by the aforementioned general formula (V) or (V'), or a salt thereof, or a solvate thereof. A compound wherein R is phenyl, and n is 1, or a salt thereof, or a solvate thereof is a preferred embodiment of this invention.

Effect of the Invention

The (S)-isomer compound (III) has superior PCSK9 protein amount-reducing action and LDL receptor amount-increasing action, and has superior blood LDL cholesterol-reducing action. Therefore, the compound is useful as, for example, an active ingredient of a medicament for reducing blood LDL cholesterol, and the like.

Further, the (S)-isomer compound (III) is also useful as an active ingredient of a medicament for prophylactic and/or therapeutic treatment of a disease in which PCs are involved, more specifically, cancer, obesity, diabetes, Alzheimer disease, or viral infectious diseases.

Further, according to the preparation method of the present invention, a desired enantiomer of the racemate compound (I) ((S)-isomer compound (III) or (R)-isomer compound (II)) can be conveniently prepared in a substantially optically pure form. For example, the method can be preferably used as a method for preparing substantially optically pure (S)-isomer compound (III), which is useful as an active ingredient of a medicament, or the like.

Modes For Carrying Out The Invention

In the specification, the term "substantially optically pure" means that optical purity of a compound is 90% ee or higher, preferably 95 to 100% ee, most preferably 97 to 100% ee.

Therefore, for example, "substantially optically pure (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid", "substantially optically pure levorotatory enantiomer of trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid" and "substantially optically pure (S)-isomer compound (III)" mean the (S)-isomer compound (III) having an optical purity of 90% ee or higher, preferably 95 to 100% ee, most preferably 97 to 100% ee.

In the present invention, optical purity of the (S)-isomer compound (III) is preferably 98% ee or higher, most preferably 99% ee or higher, as determined under the chiral HPLC analytic conditions described in Example 1.1 mentioned later, from a viewpoint of obtaining favorable PCSK9 protein amount-reducing action and/or LDL receptor amount-increasing action. If the aforementioned optical purity is achieved, the (S)-isomer compound (III) becomes to not substantially contain the other enantiomer ((R)-isomer compound (II)).

In the specification, the term "$C_{1-6}$ alkyl group" means a linear or branched alkyl group having 1 to 6 carbon atoms, and examples include, for example, methyl group, ethyl group, n-propyl group, isopropyl group, n-butyl group, isobutyl group, sec-butyl group, tert-butyl group, n-pentyl group, isopentyl group, neopentyl group, n-hexyl group, isohexyl group, and the like.

In the specification, the "$C_{6-10}$ aryl" moiety of the "$C_{6-10}$ aryl group which may have a substituent" means an aromatic hydrocarbon group having 6 to 10 carbon atoms, and examples include, for example, phenyl group, naphthyl group, azulenyl group, and the like.

In the specification, the "5- to 10-membered heteroaryl" moiety of the "5- to 10-membered heteroaryl group which may have a substituent" means a 5- to 10-membered monocyclic, polycyclic or condensed ring type aromatic heterocyclic group containing 1 to 4 heteroatoms selected from oxygen atom, sulfur atom and nitrogen atom as ring-constituting atoms. Examples include, for example, furyl group, thienyl group, pyrrolyl group, oxazolyl group, isoxazolyl group, thiazolyl group, isothiazolyl group, imidazolyl group, pyrazolyl group, oxadiazolyl group, thiadiazolyl group, triazolyl group, tetrazolyl group, pyridyl group, pyrimidyl group, pyrazinyl group, pyridazinyl group, benzofuranyl group, isobenzofuranyl group, benzothienyl group, indolyl group, isoindolyl group, indazolyl group, benzimidazolyl group, benzoxazolyl group, benzisoxazolyl group, benzothiazolyl group, benzisothiazolyl group, benzoxadiazolyl group, benzothiadiazolyl group, benzotriazolyl group, quinolyl group, isoquinolyl group, cinnolinyl group, quinazolinyl group, quinoxalinyl group, phthalazinyl group, naphthyridinyl group, purinyl group, pteridinyl group, furopyridyl group, thienopyridyl group, pyrrolopyridyl group, oxazolopyridyl group, thiazolopyridyl group, imidazopyridyl group, and the like.

In the specification, examples of the substituent of the "$C_{6-10}$ aryl group which may have substituent", and "5- to 10-membered heteroaryl group which may have a substituent" include, for example, a halogen atom, carboxyl group, carbamoyl group, sulfonyl group, sulfamoyl group, nitro group, and the like. Number of the substituent is from 1 to the maximum substitutable number, and the groups may generally have 1 to 5 substituents. As the halogen atom, any of fluorine atom, chlorine atom, bromine atom, and iodine atom may be used.

In the general formulas, the $C_{6-10}$ aryl group which may have a substituent as R is preferably phenyl group.

In the general formulas, the integer as n is preferably 1.

In the general formulas, the $C_{1-6}$ alkyl group as $R^1$ is preferably a $C_{1-4}$ alkyl group, more preferably ethyl group.

In the general formulas, the halogen atom as X is preferably chlorine atom or bromine atom, more preferably bromine atom.

In the present invention, examples of salt of each compound (for example, the O-isomer compound (III), a compound represented by the general formula (IV), a compound represented by the general formula (V), a compound represented by the general formula (V'), and the like) include, for example, acid addition salts, base addition salts, and the like, and the salt is not particularly limited so long as a pharmaceutically acceptable salt is used. Specifically, examples of the acid addition salts include acid addition salts with an inorganic acid such as hydrochloride, hydrobromide, hydroiodide, sulfate, nitrate, and phosphate; and acid addition salt with an organic acid such as benzoate, methanesulfonate, ethanesulfonate, benzenesulfonate, p-toluenesulfonate, maleate, fumarate, tartrate, citrate, and acetate. Examples of the base addition salts include base addition salts with a metal such as sodium salt, potassium salt, lithium salt, calcium salt and magnesium salt; salts with an amine such as ammonia, trimethylamine, triethylamine, pyridine, collidine, and lutidine; base addition salts with an organic base such as lysine and arginine, and the like.

In the present invention, examples of the solvent forming a solvate of each compound (for example, the (S)-isomer compound (III), a compound represented by the general formula (IV), a compound represented by the general formula (V), a compound represented by the general formula (V'), and the like) or a salt thereof include water and physiologically acceptable organic solvents, for example, ethanol, hexane, ethyl acetate, and the like, but are not limited to these examples. Examples of the active ingredient of the medicament of the present invention include, for example, hydrates and the like, but are not limited to these examples.

An example of the method for preparing substantially optically pure (S)-isomer compound (III) of the present invention is shown in Scheme 3 mentioned below, and an example of the method for preparing substantially optically pure (R)-isomer compound (II) of the present invention is shown in Scheme 4 mentioned below (in the following schemes, R, $R^1$, X, and n have the same meanings as those defined above).

Scheme 3
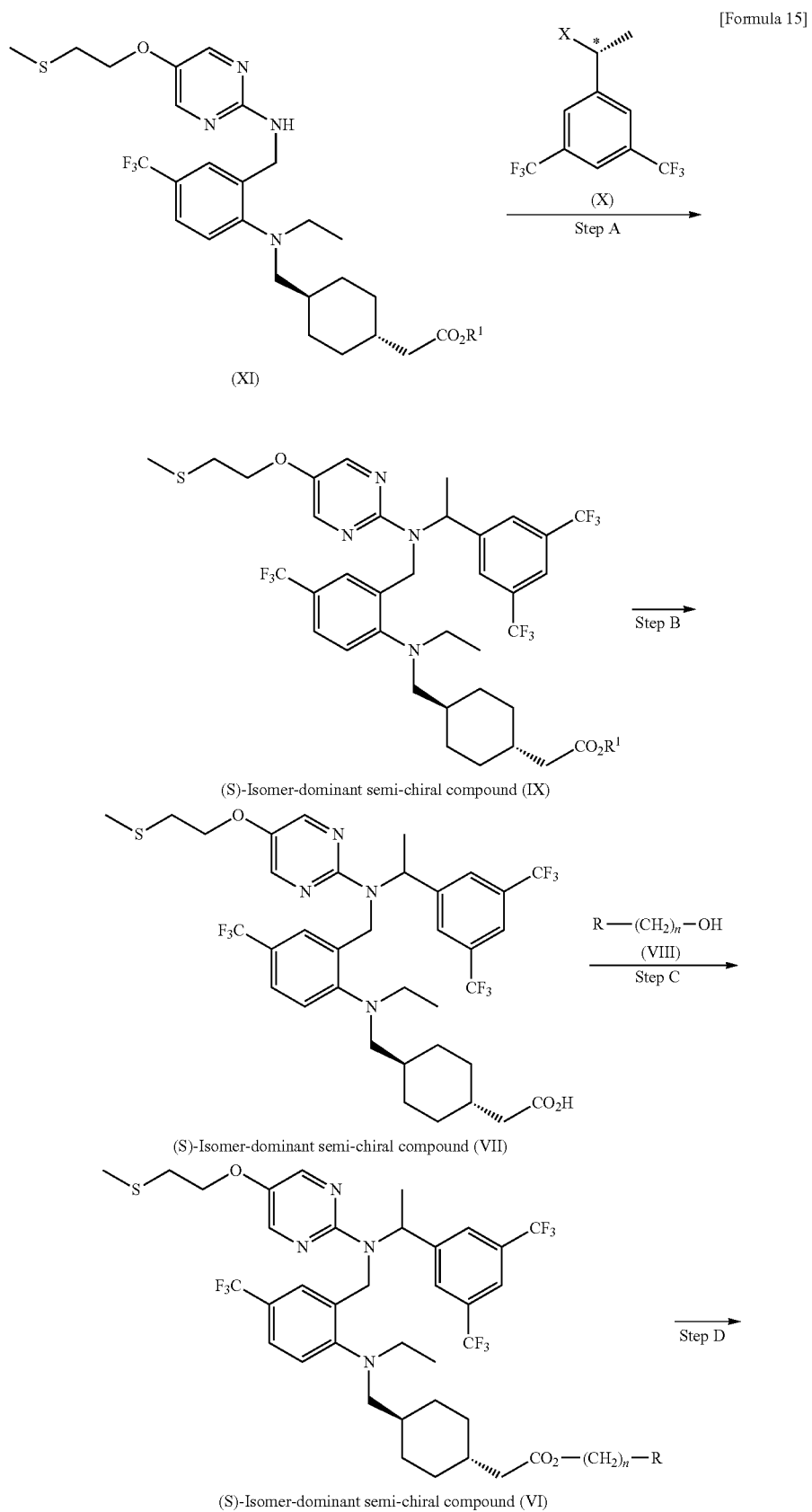

-continued
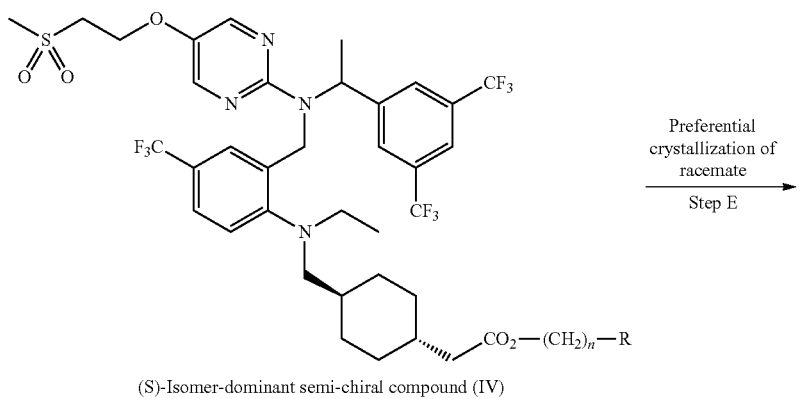
(S)-Isomer-dominant semi-chiral compound (IV)
Preferential crystallization of racemate
Step E →
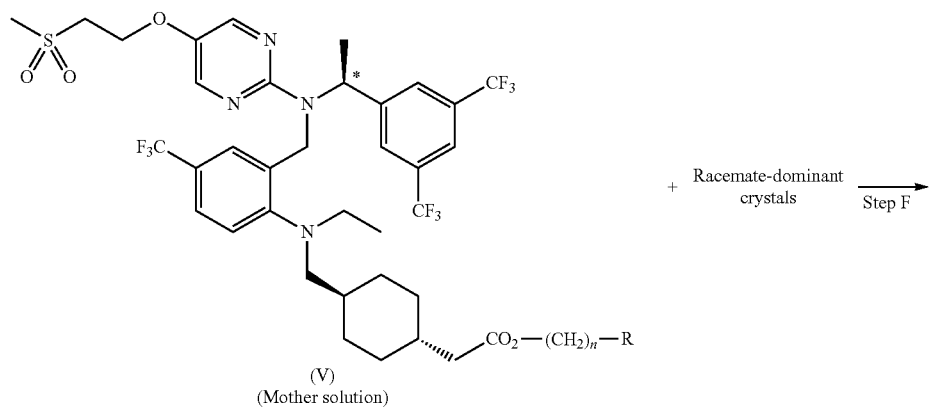
(V)
(Mother solution)
+ Racemate-dominant crystals  Step F →
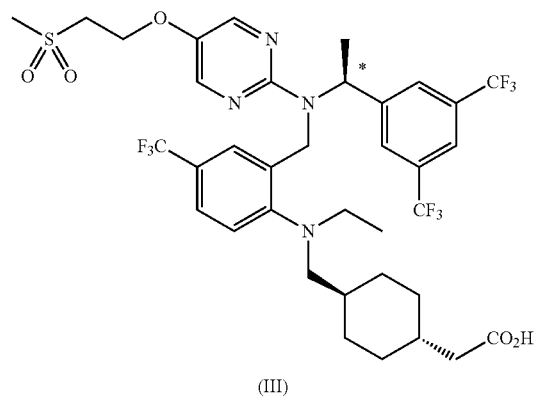
(III)

Scheme 4
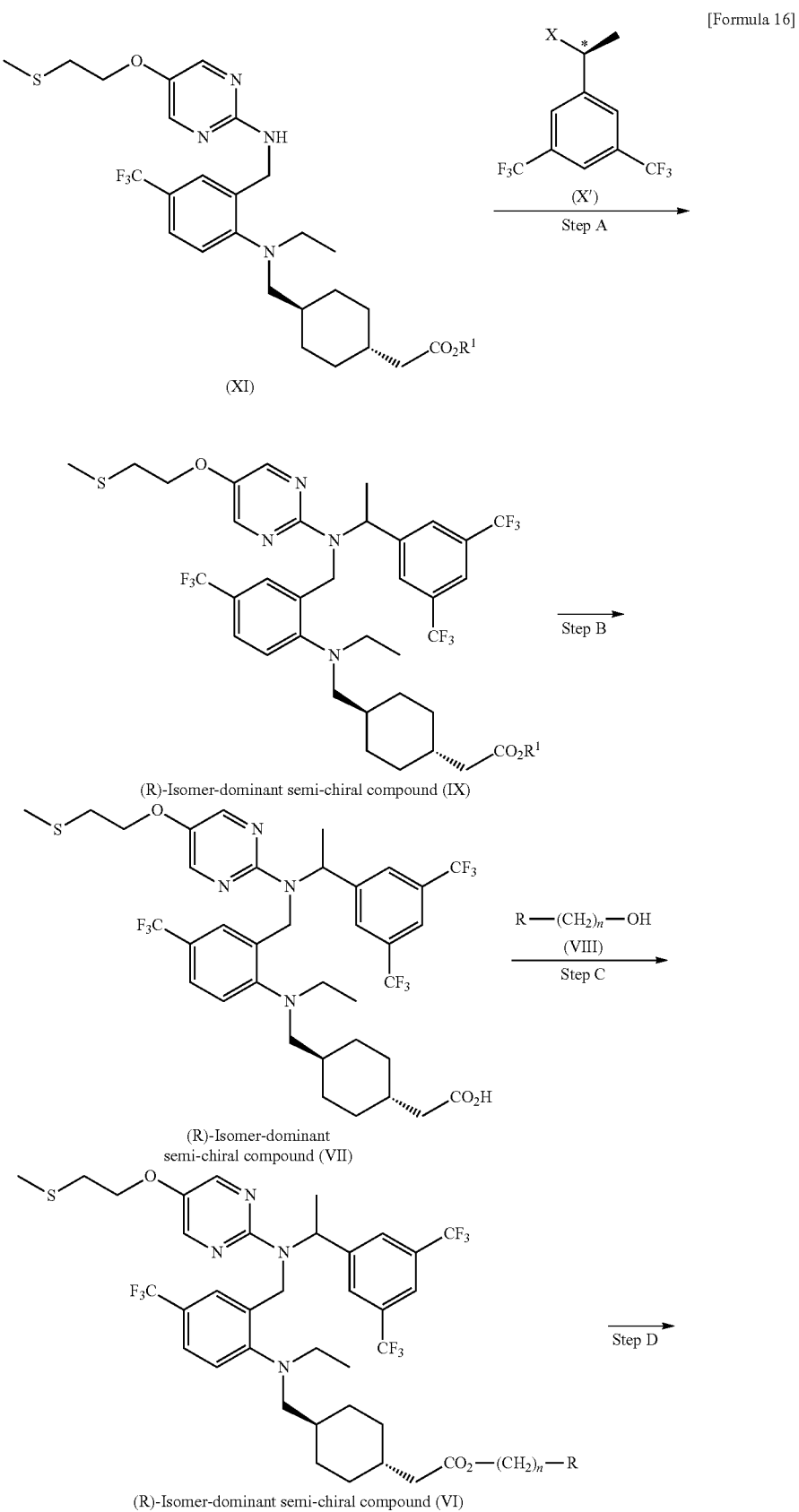

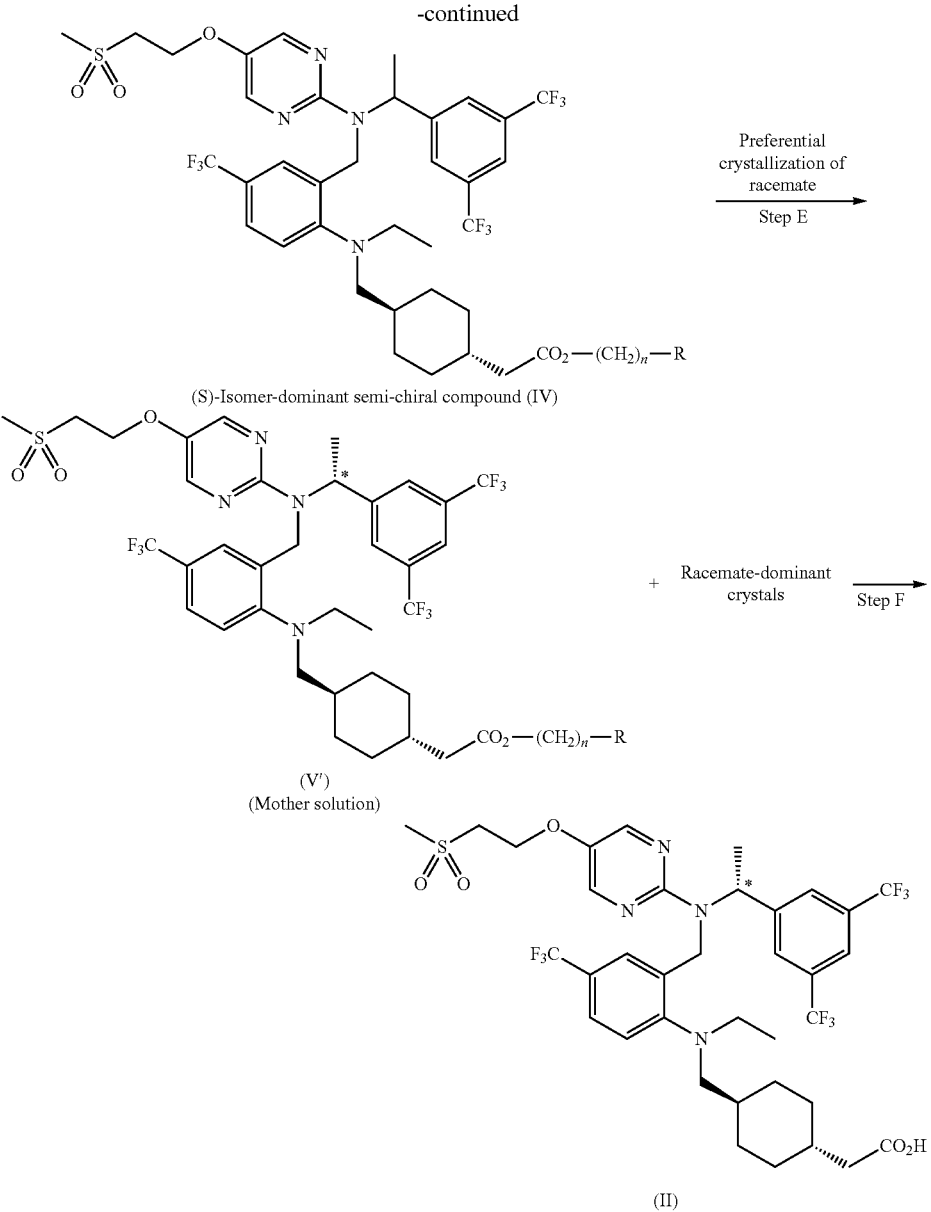

(S)-Isomer-dominant semi-chiral compound (IV)

+ Racemate-dominant crystals → Step F (V')
(Mother solution)

(II)

<Step A>

This step is to react an amine (XI) with an optically active benzyl halide (X) or (X') in the presence of a base to prepare a semi-chiral compound (IX). The compound (X) or (X') may be used in an amount of 1.0 to 3.0 molar equivalents, preferably 1.5 to 2.5 molar equivalents, based on the compound (XI).

The amine (XI) is a known compound, and the preparation method thereof is described in, for example, Patent document 2.

This reaction can be performed in a solvent in the presence of a base. The solvent is not particularly limited. For example, N,N-dimethylformamide, N-methylpyrrolidone, dimethyl sulfoxide, dioxane, tetrahydrofuran, acetonitrile, propionitrile, and the like can be used alone or in combination. Preferred examples of the solvent include tetrahydrofuran, N,N-dimethylformamide, and mixed solvents of these. The volume of the solvent is not particularly limited. The solvent may be used in a 2- to 20-fold amount (V/W), preferably 5- to 12-fold amount (V/W), more preferably 7- to 10-fold amount (V/W), based on the compound (XI).

The base is not particularly limited. For example, alkali metal hydrides such as lithium hydride, sodium hydride, and potassium hydride; alkali metals such as metal lithium, metal sodium, and metal potassium; alkali metal hydroxides such as lithium hydroxide, sodium hydroxide, and potassium hydroxide; alkali metal carbonates such as lithium carbonate, sodium carbonate, potassium carbonate, and cesium carbonate; alkali metal amides such as lithium diisopropylamide, sodium diisopropylamide, potassium diisopropylamide, lithium hexamethyldisilazide, sodium hexamethyldisilazide, and potassium hexamethyldisilazide; alkoxyalkali metals such as t-butoxysodium, and t-butoxypotassium; and organic lithium compounds such as n-butyllithium, s-butyllithium, and t-butyllithium can be used. Preferred examples of the base include alkali metal hydrides, and a more preferred example is sodium hydride. The base may be used in an amount of 1.0 to 5.0 molar equivalent, preferably 2.0 to 4.0 molar equivalents, based on the compound (XI).

The reaction temperature is generally in the range of −80 to 100° C., preferably −30 to 50° C., more preferably −20 to 5° C. The reaction time is generally 5 minutes to 48 hours, preferably 30 minutes to 24 hours, more preferably 3 to 8 hours. In this reaction, it is preferable to use substantially optically pure benzyl halide (X) or (X'). By this reaction, racemization partially advances, and the semi-chiral compound (IX) is obtained. This semi-chiral compound (IX) can be used for the next step without any treatment. Optical purity is substantially maintained through Steps B to D, and the semi-chiral compound (IV) having an optical purity comparable to that of the semi-chiral compound (IX) can be obtained. According to the study by the inventors of the present invention, even if the reaction with the optically active benzyl halide (X) or (X') is performed in this step by using the amine (XI) wherein $R^1$ is benzyl group, the semi-chiral compound (IX) as the objective compound cannot be obtained in a satisfactory yield, but if a $C_{1-6}$ alkyl group is used as $R^1$, the desired semi-chiral compound (IX) can be obtained in a sufficient yield.

<Step B>

This step is to hydrolyze the semi-chiral compound (IX) to prepare a semi-chiral compound (VII).

This reaction can be performed in a solvent in the presence of a base. Although the solvent is not particularly limited, for example, alcohols such as methanol, ethanol, propanol, isopropanol, and tert-butanol, acetonitrile, tetrahydrofuran, dimethyl sulfoxide, N,N-dimethylformamide, N-methylpyrrolidone, dioxane, water, and the like can be used alone or in combination. Preferred examples of the solvent include a combination of an alcohol and water, and more preferred examples of the solvent include a combination of ethanol and water. Although the volume of the solvent is not particularly limited, the solvent can be used in a 10- to 100-fold amount (V/W), preferably 20- to 50-fold amount (V/W), more preferably 30- to 40-fold amount (V/W), based on the compound (IX).

The base is not particularly limited. For example, alkali metal hydroxides such as lithium hydroxide, sodium hydroxide, and potassium hydroxide; alkali metal carbonates such as lithium carbonate, sodium carbonate, potassium carbonate, and cesium carbonate; quaternary ammonium hydroxides such as tetramethylammonium hydroxide, tetraethylammonium hydroxide, tetrapropylammonium hydroxide, tetrabutylammonium hydroxide, and benzyltrimethylammonium hydroxide (Triton B), and the like can be used. Preferred examples of the base include alkali metal hydroxides, and more preferred examples include sodium hydroxide. The base may preferably be used in an amount of 1.0 to 5.0 molar equivalents, more preferably 2.0 to 3.0 molar equivalents, based on the compound (IX).

The reaction temperature is generally in the range of 0 to 100° C., preferably 30 to 80° C., more preferably 40 to 60° C. The reaction time is generally preferably 5 minutes to 48 hours, more preferably 30 minutes to 12 hours, most preferably 2 to 5 hours.

<Step C>

This step is to condense the semi-chiral compound (VII) and an alcohol (VIII) to prepare a semi-chiral compound (VI). The alcohol (VIII) can be used in an amount of 0.8 to 2.0 molar equivalents, preferably 1.0 to 1.2 molar equivalents, based on the compound (VII).

This reaction can be performed by using a condensing agent in a solvent in the presence or absence of a base. The reaction may be performed in the presence of a condensation accelerator. Although the solvent is not particularly limited, for example, halogenated hydrocarbons such as 1,2-dichloroethane, chloroform, and dichloromethane; acetic acid esters such as ethyl acetate, and isopropyl acetate; aromatic hydrocarbons such as toluene, and benzene; tetrahydrofuran, dioxane, acetonitrile, propionitrile, and the like can be used. Preferred examples of the solvent include halogenated hydrocarbons, and more preferred examples include dichloroethane. Although the volume of the solvent is not particularly limited, the solvent can be used in a 5- to 100-fold amount (V/W), preferably 10- to 20-fold amount (V/W), based on the compound (VII).

The base is not particularly limited. For example, organic bases such as pyridine, 4-dimethylaminopyridine (DMAP), collidine, lutidine, 1,8-diazabicyclo[5.4.0]undec-7-ene (DBU), 1,5-diazabicyclo[4.3.0]non-5-ene (DBN), 1,4-diazabicyclo[2.2.2]octane (DABCO), triethylamine, diisopropylethylamine, diisopropylpentylamine, and trimethylamine; alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alkali metal bicarbonates such as sodium hydrogencarbonate, and potassium hydrogencarbonate, and the like can be used.

Although the condensation accelerator is not particularly limited, DMAP, 1-hydroxy-7-azabenzotriazole (HOAt), 1-hydroxybenzotriazole (HOBt), 3,4-dihydro-3-hydroxy-4-oxo-1,2,3-benzotriazine (HODhbt), N-hydroxy-5-norbornene-2,3-dicarboxylmide (HONB), pentafluorophenol (HOPfp), N-hydroxyphthalimide (HOPht), N-hydroxysuccinimide (HOSu), and the like can be used. As the condensation accelerator, DMAP is preferred. The condensation accelerator may be used in an amount of 0.001 to 1.0 molar equivalent, preferably 0.05 to 0.5 molar equivalent, based on the compound (VII).

Although the condensing agent is not particularly limited, Dicyclohexylcarbodiimide (DCC), diisopropylcarbodiimide (DIPCI), N-(3-dimethylaminopropyl)-N'-ethyl-carbodiimide (commonly called water soluble carbodiimide (WSCI)), WSC.HCl, and the like can be used. As the condensing agent, WSC.HCl is preferred. The condensing agent may be used in an amount of 1.0 to 3.0 molar equivalents, preferably 1.0 to 1.2 molar equivalents, based on the compound (VII).

The reaction temperature is generally 0 to 100° C., preferably 0 to 80° C., more preferably 10 to 30° C. The reaction time is generally preferably 5 minutes to 48 hours, more preferably 30 minutes to 24 hours, most preferably 8 to 16 hours.

<Step D>

This step is to oxidize the sulfur atom of the semi-chiral compound (VI) to prepare the semi-chiral compound (IV).

As the oxidization method, ordinary methods for converting sulfur atom into sulfonyl group can be used. As the oxidizing agent, for example, aqueous hydrogen peroxide as used in oxidization reaction using a catalytic amount of sodium tungstate, molybdenum dioxide dichloride, or tantalum pentachloride, sodium perborate, Oxone (registered trademark), sodium periodate, potassium periodate, meta-chloroperbenzoic acid (mCPBA), pyridinium chlorochromate (PCC), pyridinium dichromate (PDC), N-chlorosuccinimide (NCS), N-bromosuccinimide (NBS), N-iodosuccinimide (NIS), iodine, bromine, and the like can be used. A preferred oxidizing agent is a combination of tantalum pentachloride and aqueous hydrogen peroxide. Tantalum pentachloride can be used in an amount of 0.001 to 1.0 molar equivalent, preferably 0.05 to 0.5 molar equivalent, based on the compound (VI). Aqueous hydrogen peroxide can be used in an amount of 1.0 to 10 molar equivalents, preferably 4.0 to 6.0 molar equivalents, based on the compound (VD.

The solvent is not particularly limited. Examples include, for example, water, alcohols such as methanol, ethanol, isopropanol and tert-butanol, acetonitrile, acetone, tetrahydrofuran, dichloromethane, chloroform, 1,2-dichloroethane, carbon tetrachloride, N,N-dimethylformamide, acetic acid, and the like. Preferred examples of the solvent include alcohols, and more preferred examples include 2-propanol. Although volume of the solvent is not particularly limited, the solvent may be used in a 5- to 100-fold amount (V/W), preferably 10- to 30-fold amount (V/W), based on the compound (VI).

The reaction temperature may be generally 0 to 100° C., preferably 10 to 60° C., more preferably 10 to 30° C. The reaction time is generally preferably 5 minutes to 48 hours, more preferably 30 minutes to 24 hours, most preferably 8 to 16 hours.

<Step E>
This step is to preferentially crystallize racemate-dominant crystals of low optical purity from the semi-chiral compound (IV) to prepare the optical isomer (V) or (V') with high optical purity.

This step is to crystallize racemate-dominant crystals in a solvent containing the semi-chiral compound (IV), and then to remove the resulting racemate-dominant crystals to have the optical isomer (V) or (V') with high optical purity left in the mother solution.

Examples of the solvent include alcohols such as methanol, ethanol, n-propanol, and isopropanol. Alcohols having a linear or branched chain containing 1 to 6 carbon atoms are preferred, and ethanol and isopropanol are particularly preferred. Amount of the solvent is a 2- to 20-fold amount (V/W), preferably 4- to 10-fold amount (V/W), more preferably 5- to 8-fold amount (V/W), based on the compound (IV).

The crystallization may be performed by dissolving the semi-chiral compound (IV) in the solvent, and stirring the solution at 10 to 40° C., preferably 15 to 20° C., for 30 minutes to two days, preferably 15 to 24 hours. If it is desired to increase yield of the crystals, the stirring may be then performed for 30 minutes to 24 hours, preferably 2 to 5 hours, under cooling the solution to −10 to 10° C., preferably −5 to 5° C. The racemate-dominant crystals may be crystals absolutely consisting of racemate, or they may generally be crystals of low optical purity (about 0 to 40% ee) containing about 60 to 100% of racemate components.

This step may be performed in the presence of separately prepared seed crystals of the racemate. The seed crystals of the racemate used in this process are crystals of the racemate of the compound represented by the general formula (IV). Examples include, for example, crystals of racemate of trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid benzyl ester.

Further, the racemate-dominant crystals obtained in this step E may be used as the seed crystals of racemate without any treatment. Crystal separately obtained by preparation of racemate of the compound represented by the general formula (IV) and successive crystallization may also be used as the seed crystals of the racemate. Such racemate of the compound represented by the general formula (IV) can be prepared by, for example, the method described below.

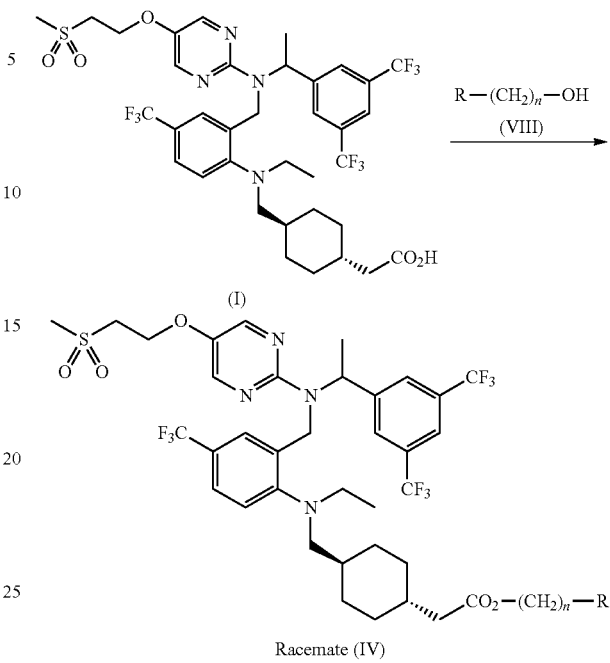

In this reaction, the racemate compound (I) and an alcohol (VIII) are condensed to prepare the racemate (IV). The alcohol (VIII) may be used in an amount of 0.8 to 2.0 molar equivalents, preferably 1.0 to 1.2 molar equivalents, based on the racemate compound (I).

This reaction can be performed in a solvent by using a condensing agent in the presence or absence of a base. The reaction may be performed in the presence of a condensation accelerator. The solvent is not particularly limited. For example, halogenated hydrocarbons such as 1,2-dichloroethane, chloroform, and dichloromethane; acetic acid esters such as ethyl acetate, and isopropyl acetate; aromatic hydrocarbons such as toluene, and benzene; tetrahydrofuran, dioxane, acetonitrile, propionitrile, and the like can be used. Preferred examples of the solvent include halogenated hydrocarbons, and more preferred examples include dichloromethane. Although the volume of the solvent is not particularly limited, the solvent can be used in a 5- to 100-fold amount (V/W), preferably 10- to 20-fold amount (V/W), based on the racemate compound (I).

The base is not particularly limited. For example, organic bases such as pyridine, 4-dimethylaminopyridine (DMAP), colidine, lutidine, 1,8-diazabicyclo[5.4.0]undec-7-ene (DBU), 1,5-diazabicyclo[4.3.0]non-5-ene (DBN), 1,4-diazabicyclo[2.2.2]octane (DABCO), triethylamine, diisopropylethylamine, diisopropylpentylamine, and trimethylamine; alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alkali metal bicarbonates such as sodium hydrogencarbonate, and potassium hydrogencarbonate, and the like can be used.

Although the condensation accelerator is not particularly limited, DMAP, 1-hydroxy-7-azabenzotriazole (HOAt), 1-hydroxybenzotriazole (HOBO, 3,4-dihydro-3-hydroxy-4-oxo-1,2,3-benzotriazine (HODhbt), N-hydroxy-5-norbornene-2,3-dicarboxyimide (HONB), pentafluorophenol (HOPfp), N-hydroxyphthalimide (HOPht), N-hydroxysuccinimide (HOSu), and the like can be used. As the condensation accelerator, DMAP is preferred. The condensation accelerator may be used in an amount of 0.001 to 1.0 molar equivalent, preferably 0.05 to 0.5 molar equivalent, based on the racemate compound (I).

Although the condensing agent is not particularly limited, dicyclohexylcarbodiimide (DCC), diisopropylcarbodiimide (DIPCI), N-(3-dimethylaminopropyl)-NLethyl-carbodiimide (commonly called water soluble carbodiimide (WSCI)), WSC.HCl, and the like can be used. As the condensing agent, WSC.HCl is preferred. The condensing agent may be used in an amount of 1.0 to 3.0 molar equivalents, preferably 1.0 to 1.2 molar equivalents, based on the racemate compound (I).

The reaction temperature is generally 0 to 100° C., preferably 0 to 80° C., more preferably 10 to 30° C. The reaction time is generally preferably 5 minutes to 48 hours, more preferably 30 minutes to 24 hours, most preferably 8 to 16 hours.

The crystallization of racemate of the compound represented by the general formula (TV) (preparation of the seed crystals of the racemate) can be performed under conditions similar to those applied to the preferential crystallization of the racemate-dominant crystals from the semi-chiral compound (IV).

More specifically, the racemate compound (IV) can be dissolved in a solvent, and the solution can be stirred at 10 to 40° C., preferably 15 to 20° C., for 30 minutes to two days, preferably 15 to 24 hours. If it is desired to increase yield of the crystals, the stirring may be further performed for 30 minutes to 24 hours, preferably 2 to 5 hours, under cooling the solution to −10 to 10° C., preferably −5 to 5° C. Examples of the solvent include alcohols such as methanol, ethanol, n-propanol, and isopropanol. Alcohols having a linear or branched chain containing 1 to 6 carbon atoms are preferred, and ethanol and isopropanol are particularly preferred. Amount of the solvent is a 2- to 20-fold amount (V/W), preferably 4- to 10-fold amount (V/W), more preferably 5- to 8-fold amount (V/W), based on the racemate compound (IV).

<Step F>

This step is to perform deprotection of the compound (V) or (V') of high optical purity to prepare substantially optically pure (S)-isomer compound (III) or (R)-isomer compound (II).

This reaction can be performed by catalytic reduction using a metal catalyst and a hydrogen source in a solvent, or a hydrolysis reaction using a base in a solvent. When the deprotection is performed by the catalytic reduction, alcohols such as methanol, ethanol, isopropanol and tert-butanol; ethers such as diethyl ether, tetrahydrofuran and dioxane; acetic acid esters such as ethyl acetate, and isopropyl acetate; acetic acid; water, and the like can be used as a solvent. As the solvent, alcohols are preferred, and ethanol is more preferred. The solvent may be used in a 5- to 30-fold amount (V/W), preferably 5- to 15-fold amount (V/W), based on the compound (V) or (V').

As the hydrogen source, for example, hydrogen, cyclohexadiene, formic acid, ammonium formate, and the like can be used. As the hydrogen source, hydrogen is preferred. As the metal catalyst, palladium/carbon, palladium black, Raney nickel, platinum dioxide, platinum black, and the like can be used. As the metal catalyst, palladium/carbon is preferred. Palladium/carbon may be used in a 0.001- to 0.5-fold amount (W/W), preferably 0.05- to 0.2-fold amount (W/W), based on the compound (V) or (V') in terms of the amount of 10% Pd—C (wet).

The catalytic reduction can generally be performed in the range of 0 to 100° C., preferably 10 to 60° C., more preferably 10 to 30° C. The reaction time is generally preferably 5 minutes to 24 hours, more preferably 30 minutes to 16 hours, most preferably 1 to 6 hours.

When the deprotection is performed by the hydrolysis reaction, for example, alcohols such as methanol, ethanol, propanol, 2-propanol, and t-butanol, acetonitrile, propionitrile, tetrahydrofuran, dimethyl sulfoxide, N,N-dimethylformamide, N-methylpyrrolidone, dioxane, water, and the like can be used alone or in combination, although the solvent is not particularly limited. As the base, for example, alkali metal hydroxides such as lithium hydroxide, sodium hydroxide, and potassium hydroxide; alkali metal carbonates such as lithium carbonate, sodium carbonate, potassium carbonate, and cesium carbonate; quaternary ammonium hydroxides such as tetramethylammonium hydroxide, tetraethylammonium hydroxide, tetrapropylammonium hydroxide, tetrabutylammonium hydroxide, and benzyltrimethylammonium hydroxide (Triton B), and the like can be used, although the base is not particularly limited.

The optically active benzyl halide (X) or (X') can be synthesized by, for example, the method described below.

[Formula 18]

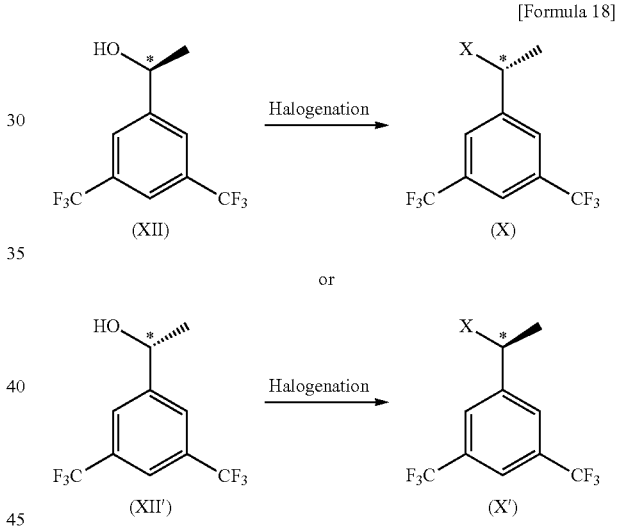

This reaction consists of the step of halogenating optically active 1-[3,5-bis(trifluoromethyl)phenyl]ethanol (XII) or (XII') in the presence of a halogenating agent to highly efficiently prepare optically active 1-halo-1-[3,5-bis(trifluoromethyl)phenyl]ethane (X) or (X') without substantially reducing the optical purity.

Examples of the halogenating agent used for this reaction include chlorinating agents such as thionyl chloride, phosphorus trichloride, phosphorus pentachloride and phosphorus oxychloride; brominating agents such as phosphorus tribromide, phosphorus tribromide and hydrogen bromide (30% solution in acetic phosphorus tribromide and pyridine, N-bromosuccinimide and methyl sulfide, N-bromosuccinimide and triphenylphosphine, 1,2-dibromo-1,1,2,2-tetrachloroethane and triphenylphosphine, bromodimethylsulfonium bromide, pyridinium bromide perbromide and hexamethyldisilane, bromine and triphenylphosphine, bromine and tributylphosphine, bromine and methyl sulfide, zinc bromide and triphenylphosphine and dimethyl azodicarboxylate, lithium bromide and chlorotrimethylsilane, lithium bromide and trifluoroacetic anhydride, bromotrimethylsilane, carbon tetrabromide and triphenylphosphine, and thionyl bromide; and iodinating agents such as hydrogen iodide, and potassium iodide and phosphoric acid. When the halogenating agent is a brominating agent, phosphorus tribromide and hydrogen bromide (30% solution in acetic acid), 1,2-dibromo-1,1,2,2-tetrachloroethane and triphenylphosphine, and N-bromosuccinimide and methyl sulfide are preferred.

The reaction using phosphorus tribromide and hydrogen bromide as the halogenating agent, and the reaction using 1,2-dibromo-1,1,2,2-tetrachloroethane and triphenylphosphine as the halogenating agent will be, in particular, specifically explained below.

<Reaction Using Phosphorus Tribromide and Hydrogen Bromide (30% Solution in Acetic Acid) as Halogenating Agent>

When phosphorus tribromide and hydrogen bromide (30% solution in acetic acid) are used as the halogenating agent, phosphorus tribromide is used in an amount of 0.3 to 2.0 molar equivalents, preferably 0.4 to 0.6 molar equivalent, based on the phenylethanol (XII) or (XII'). Hydrogen bromide is used in an amount of 0.7 to 3.0 molar equivalents, preferably 0.8 to 1.2 molar equivalents, based on the phenylethanol (XII) or (XII').

This reaction can be performed in the presence or absence of a solvent. When the reaction is performed in the presence of a solvent, the solvent to be used is not particularly limited so long as the solvent does not participate in the reaction. Examples include, for example, aromatic hydrocarbons such as benzene, toluene, xylene, mesitylene, chlorobenzene, 1,2-dichlorobenzene, and nitrobenzene; aliphatic hydrocarbons such as n-pentane, n-hexane, cyclohexane, n-heptane, n-octane, and n-decane; halogenated hydrocarbons such as methylene chlorid, 1,2-dichloroethane, chloroform, and carbon tetrachloride, and the like. Among them, benzene, toluene, xylene, methylene chloride, 1,2-dichloroethane, n-pentane, n-hexane, and n-heptane are preferred, and especially, toluene, methylene chloride, and n-heptane are more preferred. These solvents can be used alone or in combination, and the amount of the solvent to be used is not particularly limited.

The reaction temperature may be generally in the range of −50 to 150° C., more preferably −20 to 80° C., most preferably 0 to 15° C. Generally, the reaction time is preferably 5 minutes to 48 hours, more preferably 30 minutes to 36 hours, most preferably 12 to 24 hours.

<Reaction Using 1,2-dibromo-1,1,2,2-tetrachloroethane and triphenylphosphine as Halogenating Agent>

When 1,2-dibromo-1,1,2,2-tetrachloroethane and triphenylphosphine are used as the halogenating agent, 1,2-dibromo-1,1,2,2-tetrachloroethane is used in an amount of 1.0 to 3.0 molar equivalents, preferably 1.0 to 1.2 molar equivalents, based on the phenylethanol (XII) or (XII'). Triphenylphosphine is used in an amount of 1.0 to 3.0 molar equivalents, preferably 1.0 to 1.2 molar equivalents, based on the phenylethanol (XII) or (XII').

This reaction can be performed in the presence of a solvent. The solvent to be used is not particularly limited so long as the solvent that does not participate in the reaction. Examples include, for example, aromatic hydrocarbons such as benzene, toluene, xylene, mesitylene, chlorobenzene, 1,2-dichlorobenzene, and nitrobenzene; aliphatic hydrocarbons such as n-pentane, n-hexane, cyclohexane, n-heptane, n-octane, and n-decane; halogenated hydrocarbons such as methylene chloride, 1,2-dichloroethane, chloroform, and carbon tetrachloride, and the like. Preferred examples of the solvent include aromatic hydrocarbons or halogenated hydrocarbons, more preferred examples include benzene, toluene, xylene, methylene chloride, and 1,2-dichloroethane, and particularly preferred examples include toluene, methylene chloride, and 1,2-dichloroethane. These solvents can be used alone or in combination. Although the volume of the solvent is not particularly limited, the solvent can be used in a 1- to 10-fold amount (V/W), preferably 2- to 4-fold amount (V/W), nn the base phenylethanol (XII) or (XII').

The reaction temperature may be generally in the range of −50 to 150° C., more preferably −20 to 80° C., most preferably 0 to 30° C. Generally, the reaction time is preferably 5 minutes to 48 hours, more preferably 30 minutes to 36 hours, most preferably 1 to 2 hours.

The (S)-isomer compound (III), or a salt thereof, or a solvate thereof has suppressing action against PCSK9 mRNA expression as specifically demonstrated in the examples described below. The substance also has reducing action on PCSK9 protein amount and increasing action on LDL receptor amount, and has an action of reducing blood LDL cholesterol in vivo.

Although the present invention is not bound by the following estimation, it is estimated that the (S)-isomer compound or a salt thereof, or a solvate thereof suppresses production of the PCSK9 protein, thereby suppresses decomposition of LDL receptor and increases amount of LDL receptor, and as a result, the substance promotes incorporation of blood LDLs into the LDL receptor. It is further estimated that such promotion of the incorporation of blood LDLs into the LDL receptor constitutes one of the factors for exhibiting the reducing action on blood LDL cholesterol value.

Therefore, a medicament and a pharmaceutical composition containing the (S)-isomer compound (III), or a salt thereof, or a solvate thereof as an active ingredient can be used as a medicament for prophylactic and/or therapeutic treatment of hyper-LDL cholesterolemia as well as such diseases as dyslipidemia (hyperlipidemia), arteriosclerosis, atherosclerosis, peripheral vascular diseases, hypercholesterolemia, familial hypercholesterolemia, cardiovascular functional disorders, angina pectoris, ischemia, cardiac ischemia, thrombosis, myocardial infarction, reperfusion disorders, angioplastic restenosis, and hypertension.

Further, since it is known that proprotein convertases (PCs) including PCSK9 are enzymes involved in onset, progress, aggravation and the like of cancer, obesity, diabetes, Alzheimer disease, and viral infectious diseases, use of a medicament and a pharmaceutical composition comprising the (S)-isomer compound (III), or a salt thereof, or a solvate thereof as an active ingredient can be expected as a medicament for prophylactic and/or therapeutic treatment of the aforementioned diseases in which PCs are involved.

The racemate compound (I) and the compound described in Patent document 2, Example 44 (trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid) has suppressing action against HMG-CoA reductase mRNA expression, as specifically demonstrated in the examples described below. Therefore, use of the racemate compound (I), the compound described in Patent document 2, Example 44, or an enantiomer thereof, or a salt thereof, or a solvate thereof can also be expected as a medicament for prophylactic and/or therapeutic treatment of a disease resulting from HMG-CoA reductase mRNA expression (for example, diseases accompanying production of isoprenoids (farnesylpyrophosphoric acid, geranylgeranylpyrophosphoric acid, and the like) that perform post-translational modification of various proteins such as Ras, Rho and Rac with lipids, specifically, inflammation, cancer, Alzheimer disease, osteoporosis, prostatic hypertrophy, glomerular diseases, vermination, virus infection, psoriasis, macular degeneration, and the like).

As the medicament of the present invention, the aforementioned active ingredient, per se, may be administered. Preferably, the active ingredient can be administered as a pharmaceutical composition for oral or parenteral administration producible by methods well known to those skilled in the art. Examples of pharmaceutical composition suitable for oral administration include, for example, tablets, capsules, powders, subtilized granules, granules, solutions, syrups, and the like, and examples of pharmaceutical composition suitable for parenteral administration include, for example, injections such as intravenous injections and intramuscular injections, drip infusions, suppositories, inhalants, eye drops, nasal drops, transdermal preparations, transmucosal preparations and the like, however, the pharmaceutical composition is not limited to these examples.

The aforementioned pharmaceutical composition can prepared by adding pharmacologically and pharmaceutically acceptable additives. Examples of the pharmacologically and pharmaceutically acceptable additives include, for example, excipients, binders, fillers, disintegrating agents, surfactants, lubricants, dispersing agents, buffering agents, preservatives, corrigents, perfumes, coating agents, diluents, and the like, but are not limited to these examples.

The dose of the medicament of the present invention is not particularly limited, and the dose can be suitably chosen depending on a type of a disease, purpose of administration, i.e., prophylactic use or therapeutic use, a type of the active ingredient, and the like, and the dose can also be suitably increased or decreased depending on various factors that should generally be taken into consideration, such as weight and age of a patient, symptoms, and administration route. For example, for oral administration, the medicament can be used in an amount in the range of about 0.1 to 500 mg in terms of weight of the active ingredient as a daily dose for an adult. The dose can be suitably chosen by those skilled in the art, and is not limited within the aforementioned range.

EXAMPLES

The present invention will be further explained with reference to examples. However, the present invention is not limited to these examples. The abbreviations used in the following examples have the following meanings.
s: Singlet
d: Doublet
t: Triplet
q: Quartet
m: Multiplet
br: Broad
J: Coupling constant
Hz: Hertz
$CDCl_3$: Deuterated chloroform
$^1$H-NMR: Proton nuclear magnetic resonance
IR: Infrared absorption spectrum Example 1

Establishment of Method for Preparing Substantially Optically Pure (S)-isomer Compound (III)

Example 1-1

Optical Resolution Using Chiral Column

It has been revealed that, when the following conditions were applied, each enantiomer can be separated from the racemate compound (I) prepared according to the method described in Patent document 2 (International Patent Publication WO2008/129951), Example 45, and that the conditions were usable for measurement of the optical purities of the (S)-isomer compound (III) and the (R)-isomer compound (II) by chiral HPLC analysis. The present invention thus provides a method for measuring optical purity of the racemate compound (I), the (S)-isomer compound (III), or the (R)-isomer compound (II), or a salt thereof, or a solvate thereof using the following chiral HPLC analysis conditions (especially the combination of the column and mobile phase mentioned below).
Column: CHIRALCEL OD-H
Mobile phase: hexane/ethanol/TFA=90/10/0.1
Flow rate: 1.0 mL/min
Column temperature: 40° C.
Detection wavelength: 242 nm
Retention time: first peak: 21.3 minutes ((R)-isomer), second peak: 23.7 minutes ((S)-isomer)

However, it was also found that, because the solvent of the mobile phase included in the aforementioned conditions contained EtOH and TFA, they reacted with carboxylic acid of the racemate compound (I) and/or each enantiomer to generate a decomposition product (ethyl ester compound).

Therefore, although the optical resolution using the chiral column under the aforementioned conditions was usable for measurement of optical purity (chiral HPLC analysis), it was unsuitable for preparation of each of substantially optically pure enantiomers, especially for preparation in a large scale.

Example 1-2

Method for Preparing Substantially Optically Pure (S)-isomer Compound (III) by Preferential Crystallization The outline of the method for preparing substantially optically pure (S)-isomer compound (III) by preferential crystallization performed by the inventors of the present invention is shown below as Scheme 5.

The absolute configuration of each compound was determined from the absolute configuration of (R)-1-bromo-1-[3,5-bis(trifluoromethyl)phenyl]ethane confirmed in Step 1.

Further, optical purity of (S)-isomer compound (III) ((S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid) obtained in Step 6 was determined by chiral HPLC analysis under the conditions described in the above section 1-1.

Furthermore, optical purities of 1-bromo-1-[3,5-bis(trifluoromethyl)phenyl]ethane obtained in Step 1, and trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid benzyl ester obtained in Steps 4 and 5 were determined by chiral HPLC analysis under the following conditions. The present invention thus also provides a method for measuring optical purity of each compound, or a salt thereof, or a solvate thereof, which uses the following chiral HPLC analysis conditions (especially the combination of the following column and the following mobile phase).

Chiral HPLC analysis conditions for 1-bromo-1-[3,5-bis(trifluoromethyl)phenyl]ethane
Column: CHIRALPAK AS-RH
Mobile phase: ethanol/water=60/40
Flow rate: 0.5 mL/minute
Column temperature: 25° C.
Detection wavelength: 220 nm
Retention time: first peak: 21.8 minute ((R)-isomer), second peak: 26.0 minute ((S)-isomer)
Chiral HPLC analysis conditions for trans-{4-[({2-[({1-[3,5-bis(trifluoromethyl)phenyl]ethyl}{5-[2-(methylsulfonyl)ethoxy]pyrimidin-2-}amino)methyl]-4-(trifluoromethyl)phenyl}(ethyl)amino)methyl]cyclohexyl}acetic acid benzyl ester
Column: CHIRALCEL OD-H
Mobile phase: hexane/ethanol=80/20
Flow rate: 1.0 mL/min
Column temperature: 40° C.
Detection wavelength: 242 nm
Retention time: first peak: 11.3 minutes ((R)-isomer), second peak: 13.0 minutes ((S)-isomer)

Scheme 5

[Formula 19]

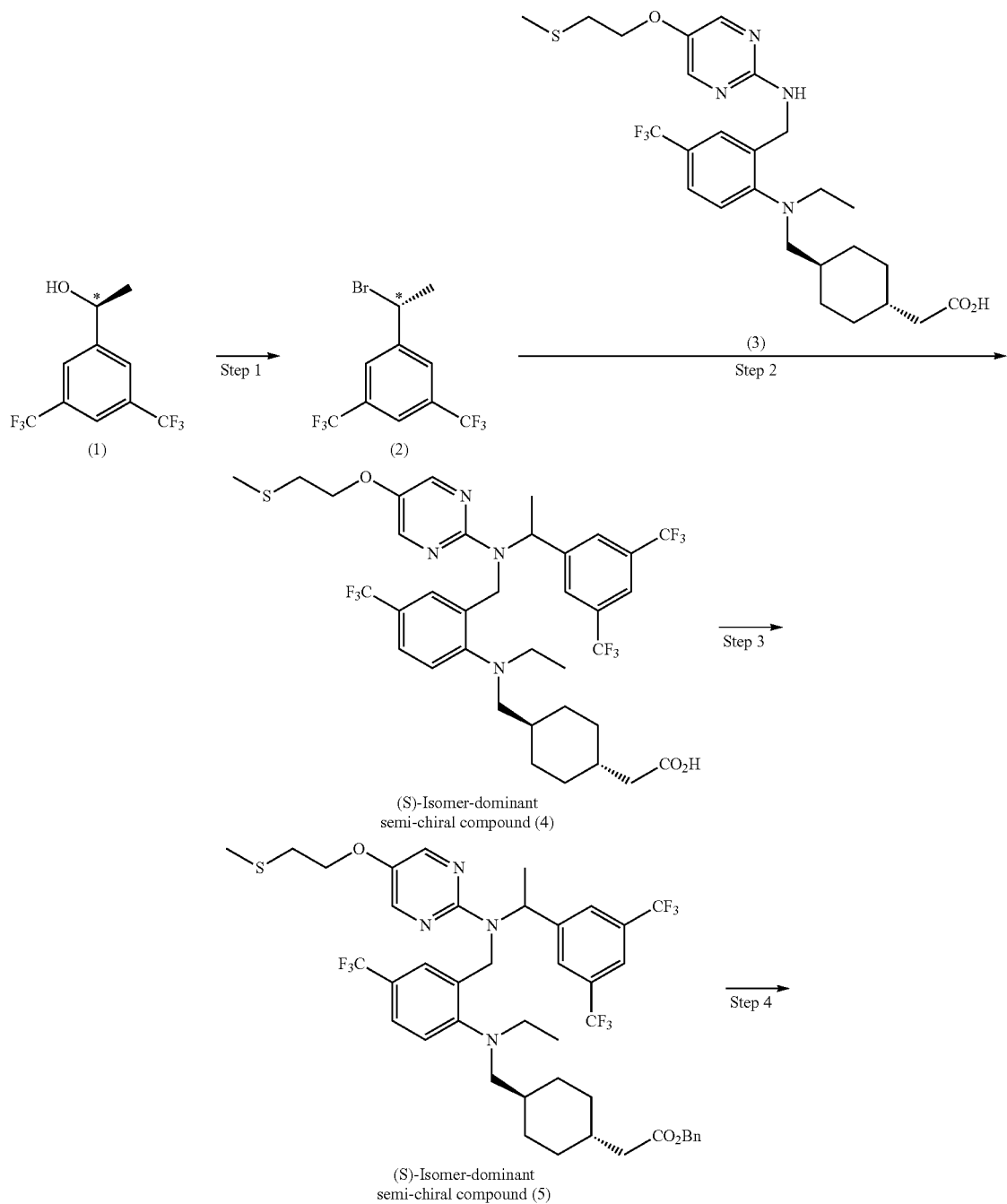

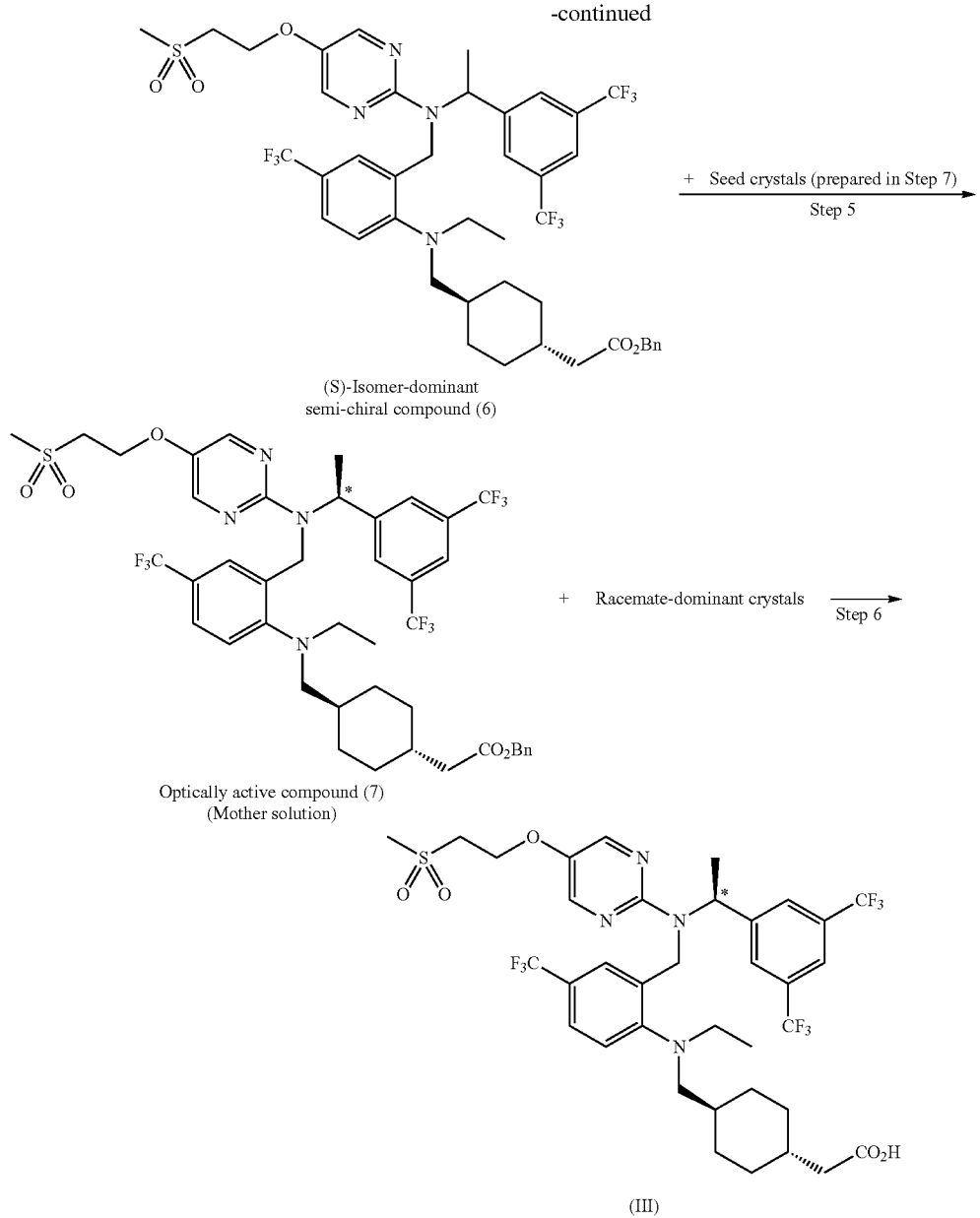

(In the scheme, Et represents ethyl group, and Bn represents benzyl group.)

Step 1: Preparation of (R)-1-bromo-1-[3,5-bis(trifluoromethyl)phenyl]ethane (R)-1-Bromo-1-[3,5-bis(trifluoromethyl)phenyl]ethane was prepared by the method described in 1-(a) mentioned below, and the absolute configuration thereof was confirmed as follows. Specifically, the confirmation was carried out by converting the resulting (R)-1-bromo-1-[3,5-bis(trifluoromethyl)phenyl]ethane into (S)-1-[3,5-bis(trifluoromethyl)phenyl]ethylamine, and comparing the sign of actually measured specific rotation thereof with that of a commercially available standard product of (S)-1-[3,5-bis(trifluoromethyl)phenyl]ethylamine of known absolute configuration.

Further, (R)-1-bromo-1-[3,5-bis(trifluoromethyl)phenyl]ethane was also prepared by the method described in 1-(b) mentioned below.

1-(a): Preparation of (R)-1-bromo-1-[3,5-bis(trifluoromethyl)phenyl]ethane (1)

Under an argon atmosphere, 1,2-dibromo-1,1,2,2-tetrachloroethane (7.57 g, 23.2 mmol) was dissolved in toluene (12.5 mL), the solution was added with triphenylphosphine (6.1 g, 23.2 mmol) at 0° C., and the mixture was stirred for 30 minutes. This reaction mixture was added dropwise with a solution of (S)-1-[3,5-bis(trifluoromethyl)phenyl]ethanol (1) (5.0 g, 19.4 mmol, >99.5% ee) in toluene (12.5 mL) at 0° C. over 10 minutes or more, and then the mixture was warmed to room temperature, and stirred for 1 hour at the same temperature. The reaction mixture was added with n-hexane (25 mL), and the mixture was filtered through Celite. The filtrate was successively washed with water, saturated aqueous sodium hydrogencarbonate, and saturated brine, dried over sodium sulfate, and then evaporated under reduced pressure. The resulting residue was distilled under reduced pressure (56° C., 0.7 mmHg) to obtain 5.52 g of (R)-1-bromo-1-[3,5-bis(trifluoromethyl)phenyl]ethane (2) as colorless oil (yield: 88.6%).

Chiral HPLC analysis: optical purify >99.5% ee (main peak: first peak), conversion rate ≥99%

$[\alpha]_D^{25}$+59.1 (c=1.03, CHCl$_3$)

$^1$H-NMR (CDCl$_3$) δ: 2.08 (3H, d, J=7.1 Hz), 5.21 (1H, q, J=7.1 Hz), 7.81 (1H, s), 7.87 (2H, s)

Confirmation of Absolute Configuration of (R)-1-bromo-1-[3,5-bis(trifluoromethyl)phenyl]ethane A solution of (R)-1-bromo-1-[3,5-bis(trifluoromethyl)phenyl]ethane (2) (106 mg, 0.336 mmol, 99% ee) obtained in 1-(a) mentioned above in N,N-dimethylformamide (1 mL) was added with sodium azide (64.4 mg, 0.990 mmol), and the mixture was stirred at −18 to −15° C. for 4 hours. The reaction solution was extracted with ethyl acetate/n-hexane (1:1) and water, the organic layer was washed with saturated brine, dried over anhydrous sodium sulfate, and then concentrated under reduced pressure to obtain 111.5 mg of 1-[3,5-bis(trifluoromethyl)phenyl]ethyl azide (crude product: 111.5 mg).

$^1$H-NMR (CDCl$_3$) δ: 1.61 (3H, d, J=6.8 Hz), 4.79 (1H, q, J=6.8 Hz), 7.78 (2H, s), 7.84 (1H, s)

The resulting 1-[3,5-bis(trifluoromethyl)phenyl]ethyl azide (crude product: 111.5 mg) was dissolved in methanol (6 mL) and the solution was added with palladium-fibroin (18 mg) for hydrogen substitution, and then the mixture was stirred at room temperature for 1 hour. The reaction mixture was filtered through Celite, the filtrate was concentrated under reduced pressure, and the resulting residue was purified by silica gel column chromatography (chloroform:methanol=50:1 to 5:1) to obtain 77.6 mg of 1-[3,5-bis(trifluoromethyl)phenyl]ethylamine as colorless oil (yield: 91%, for 2 steps).

$^1$H-NMR (CDCl$_3$) δ: 1.42 (3H, d, J=6.8 Hz), 1.58 (2H, br·s), 4.30 (1H, q, J=6.8 Hz), 7.75 (1H, s), 7.85 (2H, s)

Specific rotation of the resulting 1-[3,5-bis(trifluoromethyl)phenyl]ethylamine was as follows.

$[\alpha]_D^{25}$−15.9 (c=1.31, CHCl$_3$)

Specific rotation of a commercially available standard product ((S)-1-[3,5-b]gtrifluoromethypphenyliethylamine (Central Glass Co., Ltd., Lot. 0102000, optical purify: 99% ee)) was as follws.

$[\alpha]_D^{25}$−15.9 (c=1.15, CHCl$_3$)

The sign of the actually measured specific rotation was found to be conform with that of the commercially available standard product, and accordingly, it was confirmed that the resulting 1-[3,5-bis(trifluoromethyl)phenyl]ethylamine was the (S)-isomer. Further, because this amine was obtained from 1-bromo-1-[3,5-bis(trifluoromethyl)phenyl]ethane through a nucleophilic substitution reaction of azide ion, it was confirmed that 1-bromo-[3,5-bis(trifluoromethyl)phenyl]ethane obtained in 1-(a) mentioned above was the (R)-isomer.

1-(b): Preparation of (R)-1-bromo-1-[3,5-bis(trifluoromethyl)phenyl]ethane (2)

Under argon atmosphere, (S)-[3,5-bis(trifluoromethyl)phenyl]ethanol (1) (300 g, 1.16 mol, 96% ee) was added dropwise with phosphorous tribromide (157.3 g, 0.58 mol) at a temperature lower than 20° C. on a water bath, and the mixture was stirred at 19 to 22° C. for 30 minutes. The reaction mixture was cooled, and added dropwise with hydrogen bromide (30% solution in acetic acid, 228 mL, 1.16 mol) at a temperature lower than 0° C., and the mixture was stirred at 13 to 15° C. for 16 hours. The reaction mixture was poured into ice water, and the mixture was extracted with n-hexane (3 L×2). The organic layers were combined, successively washed with saturated aqueous sodium hydrogencarbonate (3 L), and saturated brine (3 L), dried over anhydrous magnesium sulfate, and then concentrated under reduced pressure (90 to 100 mmHg) to obtain 389.2 g of a crude product. The resulting crude product was purified by column chromatography (silica gel: 900 g, developing solvent: n-hexane) to obtain 349.8 g of (R)-1-bromo-1-[3,5-bis(trifluoromethyl)phenyl]ethane (2) as colorless oil (yield: 93.8%).

The first peak was observed as the main peak in the chiral HPLC analysis as described below, and accordingly, it was confirmed that 1-bromo-1-[3,5-bis(trifluoromethyl)phenyl]ethane prepared in 1-(b) was also the (R)-isomer, like that obtained in 1-(a).

Chiral HPLC analysis: optical purify: >93.9% ee (main peak: first peak), conversion rate: 97.8%

$^1$H-NMR (CDCl$_3$) δ: 2.08 (3H, d, J=7.1 Hz), 5.21 (1H, q, J=7.1 Hz), 7.81 (1H, s), 7.87 (2H, s)

Step 2: Preparation of (S)-isomer-dominant semi-chiral compound of trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid Under argon atmosphere, a solution of ethyl trans-[4-([(ethyl){2-[({5-[2-(methylthio)ethoxy]pyrimidin-2-yl}amino)methyl]-4-(trifluoromethyl)phenyl}amino]methyl)cyclohexyl]acetate (3) (565.4 g, 0.99 mol) synthesized by the method described in Patent document 2 (International Patent Publication WO2008/129951) in anhydrous tetrahydrofuran (THF, 2.26 L) was added with NaH (60% in oil, 119 g, 2.98 mol) under ice cooling, and the mixture was stirred at room temperature for 1 hour. The reaction mixture was cooled to −30° C., and added dropwise with a solution of (R)-1-bromo-1-[3,5-bis(trifluoromethyl)phenyl]ethane (2) (682 g, 1.99 mol, 93.9% ee) obtained in Step 1 in anhydrous N,N-dimethylformamide (4.53 L) so that temperature of the inside of the reaction system was maintained to be −15° C. or lower, and the mixture was stirred at −15 to −1° C. for 5 hours. The reaction mixture was poured into a mixed solution of ice water (35 L) and toluene (30 L), the mixture was added with citric acid up to pH being 6.9, and the organic layer was separated.

The aqueous layer was extracted twice with toluene (20 L), the organic layers were combined, dried over anhydrous magnesium sulfate, and then concentrated under reduced pressure to obtain a crude product. The crude product was dissolved in ethanol (8 L), the solution was added with 2 M aqueous NaOH (1.24 L, 2.48 mol) under ice cooling, and the mixture was stirred at 50° C. for 3.5 hours. The reaction mixture was added with 1 M aqueous HCl under ice cooling up to pH of the mixture being 5.4, the mixture was poured into water (25 L), and the mixture was extracted twice with ethyl acetate (22 L). The organic layer was washed with saturated brine (12 L), dried over anhydrous magnesium sulfate, and then concentrated under reduced pressure, and the resulting residue was purified by column chromatography (silica gel: 21 g, developing solvent: heptane/acetone=7/1→3/1) to obtain a semi-chiral compound (4) of trans-{4-[({2-[({1-[3,5-bis(trifluoromethyl)phenyl]ethyl}{5-[2-(methylthio)ethoxy]

pyrimidin-2-yl}amino)methyl]4-(trifluoromethyl)phenyl} (ethyl)amino)methyl]cyclohexyl}acetic acid (yellow oil, 744.1 g, yield: 96%).

(R)-1-Bromo-1-[3,5-bis(trifluoromethyl)phenyl]ethane (2) of which absolute configuration was confirmed as described in Step 1 mentioned above was used as the starting material, and the nucleophilic substitution reaction with the amine (3) advanced. Accordingly, the resulting semi-chiral compound (4) was an (S)-isomer dominant compound.

$^1$H-NMR (CDCl$_3$) δ: 0.85-0.96 (7H, m), 1.35-1.45 (4H, m), 1.60-1.78 (5H, m), 2.18-2.21 (5H, m), 2.69 (1H, m), 2.81-2.91 (5H, m), 4.16 (2H, q, J=6.8 Hz), 4.61 (1H, d, J=17.1 Hz), 4.85 (1H, d, J=17.1 Hz), 6.22 (1H, q, J=6.8 Hz), 7.11 (1H, d, J=8.6 Hz), 7.23 (1H, s), 7.37 (1H, d, J=8.3 Hz), 7.70 (1H, s), 7.73 (2H, s), 8.14 (2H, s)

Step 3: Preparation of (S)-isomer-dominant semi-chiral compound of trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid benzyl ester Under argon atmosphere, a solution of the (S)-isomer-dominant semi-chiral compound (4) of trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid (744.1 g, 0.95 mol) obtained in Step 2 in anhydrous dichloroethane (11.6 L) was added with benzyl alcohol (113.1 g, 1.05 mol), WSC.HCl (200.5 g, 1.05 mol) and DMAP (11.9 g, 98 mmol) under ice cooling, and the mixture was stirred overnight at room temperature. The reaction mixture was added with water (10 L), and the mixture was extracted with chloroform (19 L, 14 L). The organic layer was washed with saturated brine (12 L), dried over anhydrous magnesium sulfate, and then concentrated under reduced pressure, and the resulting residue was purified by column chromatography (silica gel: 28 g, developing solvent: heptane/ethyl acetate=6/1) to obtain a semi-chiral compound (5) of trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid benzyl ester (yellow oil, 745.8 g, yield: 90%).

The resulting semi-chiral compound (5) was an (S)-isomer-dominant compound in the same manner as the semi-chiral compound (4).

$^1$H-NMR (CDCl$_3$) δ: 0.87-0.95 (71-1, m), 1.37 (1H.m), 1.43 (3H, d, J=7.1 Hz), 1.65-1.77 (5H, m), 2.20 (2H, d, J=6.8 Hz), 2.22 (3H, s), 2.66-2.71 (2H, m), 2.82-2.91 (4H, m), 4.15 (2H, t, J=6.6 Hz), 4.62 (1H, d, J=17.1 Hz), 4.85 (1H, d, J=17.1 Hz), 5.10 (2H, s), 6.21 (1H, q, J=7.1 Hz), 7.10 (1H, d, J=8.3 Hz), 7.22 (1H, s), 7.28-7.38 (6H, m), 7.70 (1H, s), 7.73 (2H, s), 8.14 (2H, s)

Step 4: Preparation of (S)-isomer-dominant semi-chiral Compound of trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid benzyl ester Under argon atmosphere, a solution of the (S)-isomer-dominant semi-chiral compound (5) of trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid benzyl ester (745.8 g, 0.87 mol) obtained in Step 3 in 2-propanol (15.2 L) was added with tantalum pentachloride (31.3 g, 87.3 mmol) and 30% aqueous hydrogen peroxide (496 mL, 4.38 mol), and the mixture was stirred at room temperature for 5 hours. The reaction mixture was quenched with saturated aqueous sodium hydrogensulfite (3.1 L), and added with water (15 L), and the mixture was extracted with chloroform (14 L, 12 L). The organic layer was washed with saturated brine (20 L), dried over anhydrous magnesium sulfate, and then concentrated under reduced pressure, and the resulting residue was purified by column chromatography (silica gel: 26 kg, developing solvent: heptanelethyl acetate=3/1→2/1) to obtain a semi-chiral compound (6) of trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid benzyl ester (yellow amorphous, 619.5 g, yield: 79%).

The resulting semi-chiral compound (6) was an (S)-isomer-dominant compound in the same manner as the semi-chiral compound (4) and the semi-chiral compound (5).

Chiral HPLC analysis: optical purify: 67.7% ee (main peak: second peak)

$^1$H-NMR (CDCl$_3$) δ: 0.8-7.0.96 (7H, m), 1.38 (1H, m), 1.45 (3H, d, J=7.1 Hz), 1.66-1.80 (5H, m), 2.21 (2H, d, J=6.6 Hz), 2.69 (1H, m), 2.81-2.91 (3H, m), 3.08 (3H, s), 3.44 (2H, t, J=5.4 Hz), 4.44 (2H, t, J=5.4 Hz), 4.64 (1H, d, J=17.1 Hz), 4.86 (1H, d, J=17.3 Hz), 5.10 (2H, s), 6.19 (1H, q, J=6.9 Hz), 7.12 (1H, d, J=8.3 Hz), 7.19 (1H, s), 7.30-7.39 (6H, m), 7.71 (1H, s), 7.72 (2H, s), 8.16 (2H, s)

Step 5: Preparation of Substantially Optically Pure (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid benzyl ester The (S)-isomer-dominant semi-chiral compound (6) of trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid benzyl ester (111.7 g, 123.7 mmol, 67.7% ee) obtained in Step 4 was dissolved in ethanol (825 mL), and added with separately prepared seed crystals (the racemate crystals prepared in Step 7 described below, 2.0 mg) at a temperature of 15 to 20° C., and the mixture was stirred at the same temperature for 21 hours, and at 0° C. for 3 hours. The precipitates were separated by filtration, and washed with cooled ethanol (165 mL), and then the mother solution was concentrated under reduced pressure to obtain substantially optically pure trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid benzyl ester (7) (yellow amorphous, 66.38 g, yield: 59%).

The resulting trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid benzyl ester (7) was obtained by separating racemate-dominant crystals from the (S)-isomer-dominant semi-chiral compound (6) by filtration, and therefore, the result was the (S)-isomer.

Chiral HPLC analysis: optical purify >99% ee (main peak: second peak)

[α]$_D^{20}$–42.36 (c=1.0 w/v %, CHCl$_3$)

Optical purify of the racemate-dominant crystals separated by filtration was 22% ee as determined by chiral HPLC analysis (43.39 g, yield: 39%).

Step 6: Preparation of Substantially Optically Pure (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid Under nitrogen atmosphere, a solution of (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid benzyl ester (7) (34.2 g, 37.88 mmol, >99% ee) obtained in Step 5 in ethanol (340 mL) was added with 10% Pd—C (wet, 3.4 for hydrogen substitution, and then the mixture was stirred at room temperature for 2 hours. The reaction suspension was filtered through Celite, and washed with ethanol (50 mL), and the washing solution was concentrated under reduced pressure to obtain substantially optically pure trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid (III) (white amorphous, 31.78 g, yield: 100%).

The resulting compound was a levorotatory compound as shown by the specific rotation mentioned below. Further, because the resulting compound was obtained by deprotection of the ester moiety of the (S)-isomer benzyl ester (7), the result was also the (S)-isomer.

Chiral HPLC analysis: optical purify: >99% ee (main peak: second peak)

[α]$_D^{20}$–46.68 (c=1.0, CHCl$_3$)

IR (ATR) cm$^{-1}$: 2921, 1706, 1479, 1279, 1134

$^1$H-NMR (CnCl$_3$) δ: 0.80-0.96 (7H, m), 1.38 (1H.m), 1.47, (3H, d, J=7.1 Hz), 1.65-1.77 (5H, m), 2.19 (2H, d, J=6.8 Hz), 2.72 (1H, m), 2.81-2.91 (3H, m), 3.08 (3H, s), 3.45 (2H, t, J=5.2 Hz), 4.44 (2H, q, J=5.4 Hz), 4.62 (1H, d, J=17.1 Hz), 4.86 (1H, d, J=17.4 Hz), 6.21 (1H, q, J=7.1 Hz), 7.13 (1H, d, J=83 Hz), 7.19 (1H, s), 7.38 (1H, d, J=6.6 Hz), 7.71 (1H, s), 7.73 (2H, s), 8.15 (2H, s)

Step 7: Preparation of Racemate Seed Crystals of trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid benzyl ester A solution of trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid (racemate compound (I), 20 g, 24.61 mmol) synthesized by the method described in Patent document 2 (International Patent Publication WO2008/129951), Example 45 in anhydrous dichloromethane (200 mL) was added with benzyl alcohol (2.93 g, 27.07 mmol), DMAP (300 mg, 2.46 mmol) and WSC.HCl (5.19 g, 27.07 mmol) under ice cooling, and the mixture was warmed to room temperature, and stirred for 16 hours. The reaction mixture was added with water (100 mL), and the mixture was extracted with chloroform (500 mL). The organic layer was washed with 2 M aqueous hydrochloric acid (100 mL) and saturated brine (100 mL), dried over anhydrous magnesium sulfate, and then concentrated under reduced pressure, and the resulting residue was purified by column chromatography (silica gel: 350 g, developing solvent: N-hexane/ethyl acetate=3/1→1/1) to obtain trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid benzyl ester (21.15 g, yield: 95.2%) as white amorphous.

The resulting trans-{4-[({2-[({1-[3,5-bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid benzyl ester as white amorphous (7.9 g) was dissolved in ethanol (40 mL), the mixture was stirred at room temperature for 15 hours, and the resulting precipitates were collected by filtration, washed with cooled ethanol (20 mL), and dried at 60° C. for 4 hours under reduced pressure to obtain racemate crystals of trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid benzyl ester (white crystalline powder, 6.98 g, recovery yield: 88.4%).

Example 2

Study of Influence of (S)-isomer Compound (III) on Amount of PCSK9 Protein and Amount of LDL Receptor Influence of a test compound on amount of PCSK9 protein and amount of LDL receptor was studied by adding the test compound to human hepatoma cell strain, HepG2 cells, and measuring amount of PCSK9 protein and amount of LDL receptor (LDLR) by Western blotting after culture for 48 hours.

Specifically, the HepG2 cells were inoculated on a 6-well plate at a density of 5×10$^5$ cells/well and cultured overnight, and a test compound dissolved in dimethyl sulfoxide (DMSO), or only DMSO was added to the culture medium in a 1/1000-fold amount. The cells were cultured at 37° C. for 48 hours in a CO$_2$ incubator, the culture was added with 100 µL of the RIPA buffer (50 mM Tris-HCl, pH 7.8, 150 mM NaCl, 1% NP-40, 0.5% sodium deoxycholate, 0.1% SDS, proteinase inhibitor) to disrupt the cells, and proteins were extracted. The extracted proteins were centrifuged at 10000×g, the supernatant was collected, and added with an SDS sample buffer (60 mM Tris-HCl, pH 6.8, 2% SDS, 10% glycerol, 3% mercaptoethanol), and the mixture was subjected to separation by SDS-PAGE (SDS-polyacrylamide gel electrophoresis) using 8% acrylamide gel. After completion of the separation, the proteins were fixed on a nitrocellulose membrane by using iBlot Gel Transfer System (Invitrogen), and blocked by using Block Ace (DS Pharma Biomedical, Catalog No. UK-B 80).

Detection of the PCSK9 protein, LDLR, and β-actin protein, and measurement of the amounts thereof were performed by labeling the proteins on the membrane using Anti-PCSK9 (Cayman, Catalog No. 1000718), Anti-LDLR (BioVision, Catalog No. 3839-100), and Anti-β-Actin (Sigma, Catalog No. A5316), respectively, as the primary antibody, and Anti-Rabbit IgG-HRP (Sigma, Catalog No. A0545) or Anti-Mouse IgG-HRP (Sigma, Catalog No. A4416) as the secondary antibody, reacting a chemiluminescence reagent (substrate of HRP) with the secondary antibody on the membrane, and then measuring signal intensity using Lumino Image Analyzer LAS-3000 (Fuji Photo Film). The resulting signal intensity wag numprirally evaluated by using image analysis software, Science Lab 2002 Multi Gauge (Fuji Photo Film).

The resulting measured values of the PCSK9 protein amount and the LDL receptor amount were corrected between those obtained for the sample added with a test compound and the control sample (sample added with only DMSO) using the β-actin protein amounts as index. The corrected PCSK9 protein amount and LDL receptor amount of the test compound addition sample were represented by relative values based on the PCSK9 protein amount and LDL receptor amount of the control sample, respectively, which were taken as 1.

The results are shown in Table 1.

As the test compound, the following compounds were used.

1: (S)-trans-{4-[({2-[({1-[3,5-Bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid ((S)-isomer compound (III))

The (S)-isomer compound (III) (optical purify: >99% ee) was added to the culture medium at a final concentration of 10 µM.

2: (R)-trans-{4-[({2-[({1-[3,5-Bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid ((R)-isomer compound (II))

The (R)-isomer compound (II) (optical purify: ≥98% ee) was added to the culture medium at a final concentration of 10 µM.

3: trans-{4-[({2-[({1-[3,5-Bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid (racemate compound (I))

The racemate compound (I) was added to the culture medium at a final concentration of 10 µM.

TABLE 1

| Test compound | Dose (µM, concentration in culture medium) | PCSK9 protein amount (Relative value based on value of control taken as 1) | LDL receptor amount (Relative value based on value of control taken as 1) |
| --- | --- | --- | --- |
| (S)-Isomer compound (III) | 10 | 0.28 | 1.73 |
| (R)-Isomer compound (II) | 10 | 1.05 | 0.93 |
| Racemate compound (I) | 10 | 0.68 | 0.73 |

As clearly understood from the results shown in Table 1, the (S)-isomer compound (III) markedly reduced the amount of PCSK9 protein and increased the amount of LDL receptor in comparison with the control, whilst the (R)-isomer compound (II) and the racemate compound (I) had almost no such actions. In particular, the amount of LDL receptor was remarkably increased only by the (S)-isomer compound (III) in comparison with the control.

From the above test results, it was revealed that the (S)-isomer compound (III) had the reducing action on PCSK9 protein amount and the increasing action on LDL receptor amount.

In addition, although the present invention is not bound by the following estimation, it was estimated that, because the racemate compound (I) had almost no PCSK9 protein amount-reducing action and had absolutely no LDL receptor amount-increasing action despite the fact that it contained about 50% of the (S)-isomer compound (III), the (R)-isomer compound (II) as a constituent component of the racemate compound (I) inhibited the expression of the actions of the (S)-isomer compound (III) in the racemate compound (I). It was further estimated that it is preferable to increase optical purity of the (S)-isomer compound (III) to reduce the content of the (R)-isomer compound (II) especially for enhancing the LDL receptor amount-increasing action.

Example 3

Study of Influence of (S)-isomer Compound (III) PCSK9 mRNA Expression

In order to study the mechanism of the PCSK9 protein amount-reducing action revealed in Example 2 mentioned above, a test compound was added to the HepG2 cells, and expression amount of PCSK9 mRNA was measured by quantitative real-time PCR method after culture for 24 hours.

Specifically, the HepG2 cells were inoculated on a 24-well plate at a density of $2 \times 10^5$ cells/well and cultured overnight, and then a test compound dissolved in dimethyl sulfoxide (DMSO), or only DMSO was added to the culture medium in a 1/1000-fold amount. The cells were cultured at 37° C. for 24 hours in a $CO_2$ incubator, and then added with 500 µl of ISOGEN (NIPPON GENE, Catalog No. 31-02501), and the total RNA was extracted. cDNA was synthesized from the extracted total RNA by using High Capacity cDNA Reverse Transcription Kit (Applied Biosystems, Catalog No. 4368813). Expression amount of human PCSK9 mRNA was measured by quantitative real-time PCR using primers specific to human PCSK9 (Kourimate S. et al., J. Biol. Chem., Vol. 283, p9666), and Fast SYBR Green Master Mix (Applied Biosystems, Catalog No. 4385614). As the measurement apparatus, 7900HT Fast Realtime PCR System was used.

The resulting measured values of the PCSK9 mRNA expression amount were corrected between those obtained for test compound addition samples (3 samples) and control samples (sample added with only DMSO, 3 samples) using the β-actin mRNA expression amounts as index. The corrected PCSK9 mRNA expression amount of the test compound addition samples was represented with a relative value (average±standard error) based on average of the PCSK9 mRNA expression amounts of the control samples, which was taken as 1.

The results are shown in Table 2.

As the test compound, the following compound was used.

1: (S)-trans-{4-[({2-[({1-[3,5-Bis(trifluoromethyl)phenyl]ethyl}{5-[2-(methylsulfonyl)ethoxy)pyrimidin-2-yl}amino)methyl]-4-(trifluoromethyl)phenyl}(ethyl)amino)methyl]cyclohexyl}acetic acid ((S)-isomer compound (III))

The (S)-isomer compound (III) (optical purify: >99% ee) was added to the culture medium at a final concentration of 10 µM.

TABLE 2

| Test compound | Dose (μM, concentration in culture medium) | PCSK9 mRNA expression amount (Relative value based on average value of control taken as 1) |
|---|---|---|
| (S)-Isomer compound (III) | 10 | 0.18 ± 0.13 |

From the results shown in Table 2, it was revealed that the (S)-isomer compound (III) remarkably reduced the expression amount of PCSK9 mRNA in comparison with the control.

Therefore, it was considered that at least a part of the PCSK9 protein amount-reducing action of the (S)-isomer compound (III) revealed in Example 2 was based on the PCSK9 gene expression-suppressing action, and the (S)-isomer compound (III) had a PCSK9 protein production-suppressing action.

Example 4

Study of Blood LDL Cholesterol-Reducing Action of (S)-isomer Compound (III)

(S)-trans-{4-[({2-[({1-[3,5-Bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid ((S)-isomer compound (III), optical purify: >99% ee) was suspended in a 0.5% methylcellulose solution, and orally administered repeatedly to normal hamsters (male Syrian hamsters) once a day over 14 days by using a metal probe. Four hours after the final administration, blood was collected, and plasma was obtained. Lipoproteins in the plasma were analyzed by automatic measurement using an HPLC system based on the post-labeling method according to the method described in J. Lipid. Res., 43, p805-814. Specifically, 15 μL of a plasma sample was diluted 10 times with PBS containing 1 mM EDTA, and 80 μl of the diluted sample was injected into a gel filtration column (Superose 6 column (column size: 10×300 mm), GE Healthcare Bioscience) connected to an HPLC system (liquid feeding unit: Shimadzu LC-20A System, Shimadzu). Separation was performed at a flow rate of 0.5 mL/minute and a column temperature of 40° C. by using PBS containing 1 mM EDTA as a running buffer. A cholesterol-measuring reagent (Cholesterol E-Test Wako, Wako Pure Chemical Industries) was mixed with the eluate from the column at a flow rate of 0.25 mL/minute, and the reaction was performed at 40° C. in a reaction coil (0.5 mm×15 m) with feeding the eluate. Cholesterols in the eluate obtained from the reaction coil were detected at a wavelength of 600 nm. Area ratio of the LDL fraction based on the resulting total peak area of cholesterols was calculated, and the total cholesterol amount measured beforehand by using Cholesterol E-Test Wako was multiplied by the area ratio of the LDL fraction to calculate LDL cholesterol amount.

Six normal hamsters were used for each of the control group (0.5% methylcellulose solution administration group) and the test compound administration groups (10 mg/kg body weight and 30 mg/kg body weight of (S)-isomer compound (III) administration groups). The hamsters were divided into the groups beforehand on the basis of the total plasma cholesterol value.

The amounts of LDL cholesterol in the plasma of the groups (LDL-C, mg/dl) are shown in Table 3. The symbols * and *** in Table 3 means that there were significant differences at a significance level of 5% or less ($p<0.05$) and a significance level of 0.1% or less ($p<0.001$), respectively, as determined by a multi-group comparison test (Dunnett's multiple comparison test) performed between the control group and each of the test compound administration groups. Further, the LDL cholesterol amount-reducing rate of the test compound administration group based on the control group was calculated in accordance with the following equation 1 as an LDL cholesterol-reducing rate, and indicated in terms of percentage.

LDL cholesterol-reducing rate(%)=[(Average of LDL cholesterol amount of control group−Average of LDL cholesterol amount of compound administration group)/Average of LDL cholesterol amount of control group]×100    (Equation 1)

TABLE 3

| Compound | Dose (mg/kg) | Average LDL cholesterol amount ± standard deviation (mg/dl) | LDL cholesterol-reducing rate (%) |
|---|---|---|---|
| Control | — | 50 ± 3.0 | — |
| (S)-Isomer compound (III) | 10 | 40 ± 2.6* | 20.0 |
|  | 30 | 31 ± 2.6*** | 38.0 |

From the results shown in Table 3, it was revealed that the (S)-isomer compound (III) had superior blood LDL cholesterol-reducing action.

From the test results mentioned above, it was also revealed that the (S)-isomer compound (III) is useful as an active ingredient of a medicament having a blood LDL-reducing action, and the like.

Example 5

Study of Influence of Racemate Compound (I) and the Like on HMG-CoA reductase mRNA Expression A test compound was added to the HepG2 cells and the cells were cultured for 8 hours, and then HMG-CoA reductase mRNA expression amount was measured by quantitative real-time PCR.

Specifically, the HepG2 cells were inoculated on a 24-well plate at a density of $2\times10^5$ cells/well and cultured overnight, and then a test compound dissolved in dimethyl sulfoxide (DMSO), or only DMSO was added to the culture medium in a 1/1000-fold amount. The cells were cultured at 37° C. for 8 hours in a $CO_2$ incubator, and then added with 500 μL of ISOGEN (NIPPON GENE, Catalog No. 31-02501), and the total RNA was extracted. cDNA was synthesized from the extracted total RNA by using High Capacity cDNA Reverse Transcription Kit (Applied Biosystems, Catalog No. 4368813). Expression amount of human HMG-CoA reductase mRNA was measured by quantitative real-time PCR using a set of the following primers: 5'-GGTGTTCAAGGAGCATGCAAAG-3' (SEQ ID No:1) and 5'-TGACAAGATGTCCTGCTGCCA-3' (SEQ ID No:2) specific to human HMG-CoA reductase, and Fast SYBR Green Master Mix (Applied Biosystems, Catalog No. 4385614). As the measurement apparatus, 7900HT Fast Realtime PCR System was used.

The resulting measured values of the HMG-CoA reductase mRNA expression amount were corrected between those obtained for test compound addition samples (3 samples for each compound) and control samples (sample added with only DMSO, 3 samples) using the β-actin mRNA expression amounts as index. The corrected HMG-CoA reductase mRNA expression amount of the test compound addition sample was represented with a relative value (average±standard error) based on average of the HMG-CoA reductase mRNA expression amounts of the control samples, which was taken as 1.

The results are shown in Table 4.

As the test compound, the following compounds were used.

1: trans-{4-[({2-[({1-[3,5-Bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid (racemate compound (I))

The racemate compound (I) was added to the culture medium at a final concentration of 10 μM.

2: trans-{4-[({2-[({1-[3,5-Bis(trifluoromethyl)phenyl]ethyl}{5-[2-(methylthio)ethoxy]pyrimidin-2-yl}amino)methyl]-4-(trifluoromethyl)phenyl}(ethyl)amino)methyl]cyclohexyl}acetic acid (compound described in Patent document 2, Example 44)

The compound described in Patent document 2, Example 44 was added to the culture medium at a final concentration of 10 μM.

TABLE 4

| Test compound | Dose (μM, concentration in culture medium) | HMG-CoA reductase mRNA expression amount (Relative value based on average value of control taken as 1) |
| --- | --- | --- |
| Racemate compound (I) | 10 | 0.37 ± 0.02 |
| Compound described in Patent document 2, Example 44 | 10 | 0.25 ± 0.03 |

From the results shown in Table 4, it was revealed that both the racemate compound (I) and the compound described in Patent document 2, Example 44 remarkably reduced HMG-CoA reductase mRNA expression amount in comparison with the control.

Industrial Applicability

The (S)-isomer compound (III) has a PCSK9 protein amount-reducing action, and an LDL receptor amount-increasing action, and has superior blood LDL cholesterol-reducing action. Therefore, the compound can be utilized, for example, as an active ingredient of a medicament for reducing blood LDL cholesterol, and the like, and thus can be utilized in the pharmaceutical industry.

What is claimed is:

1. Substantially optically pure (S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino) methyl]cyclohexyl}acetic acid, or a salt thereof, or a solvate thereof.

2. The compound, or a salt thereof, or a solvate thereof according to claim 1, which has an optical purity of 99% ee or higher.

3. A medicament comprising the compound, or a salt thereof, or a solvate thereof according to claim 1 as an active ingredient.

4. A method for preparing substantially optically pure (S)-trans-{4-[({2-[({1-[3,5bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic acid, or a salt thereof, or a solvate thereof, which comprises removing racemate-dominant crystals from an (S)-isomer-dominant semi-chiral compound of a compound represented by the following general formula (IV):

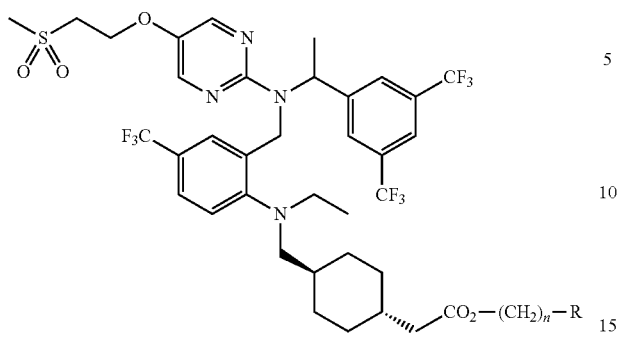

(IV)

(in the formula, R represents a $C_{6-10}$ aryl group which may have a substituent, or a 5- to 10-membered heteroaryl group which may have a substituent, and n represents an integer of 1 to 6) by preferential crystallization in a solvent to obtain a substantially optically pure compound represented by the following general formula (V):

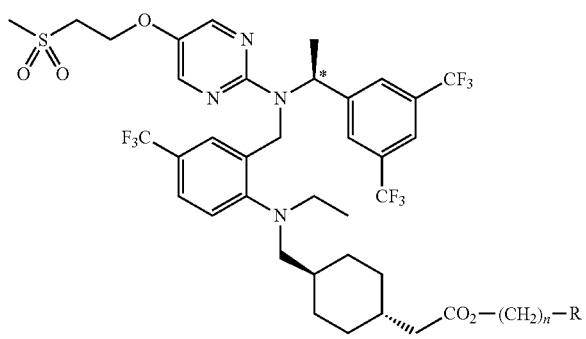

(V)

(in the formula, R and n have the same meanings as those defined above).

5. The method according to claim 4, which further comprises removing a group represented as $-(CH_2)_n-R$ from the compound represented by the general formula (V).

6. The method according to claim 4, which further comprises reacting an (S)-isomer-dominant semi-chiral compound of a compound represented by the following general formula (VI):

(VI)

(in the formula, R and n have the same meanings as those defined above) with an oxidizing agent in a solvent to prepare the (S)-isomer-dominant semi-chiral compound of a compound represented by the general formula (IV).

7. The method according to claim 6, which further comprises reacting an (S)-isomer-dominant semi-chiral compound of a compound represented by the following formula (VII):

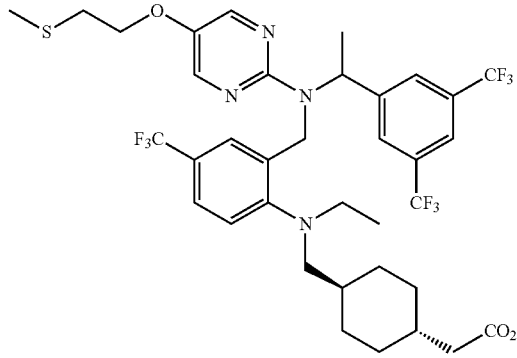

(VII)

with a compound represented by the following general formula (VIII)

$$R-(CH_2)_n-OH \quad (VIII)$$

(in the formula, R and n have the same meanings as those defined above) in a solvent in the presence of a catalyst to prepare the (S)-isomer-dominant semi-chiral compound of a compound represented by the general formula (VI).

8. The method according to claim 7, which further comprises hydrolyzing an (S)-isomer-dominant semi-chiral compound of a compound represented by the following general formula (IX):

(IX)

(in the formula, $R^1$ represents a $C_{1-6}$ alkyl group) in a solvent in the presence of a base to prepare the (S)-isomer-dominant semi-chiral compound of a compound represented by the formula (VII).

9. The method according to claim 8, which further comprises reacting a compound represented by the following general formula (X):

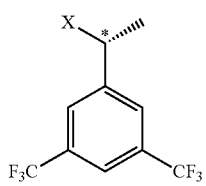

(X)

(in the formula, X represents a halogen atom), and a compound represented by the following general formula (XI):

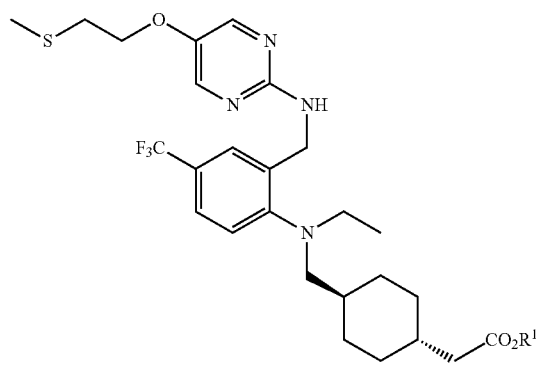

(XI)

(in the formula, $R^1$ has the same meaning as that defined above) in a solvent in the presence of a base to prepare the (S)-isomer-dominant semi-chiral compound of a compound represented by the general formula (IX).

10. The method according to claim 9, which further comprises halogenating (S)-1-[3,5-bis(trifluoromethyl)phenyl] ethanol in the presence of a halogenating agent to prepare the compound represented by the general formula (X).

11. The method according to claim 5, which further comprises reacting an (S)-isomer-dominant semi-chiral compound of a compound represented by the following general formula (VI):

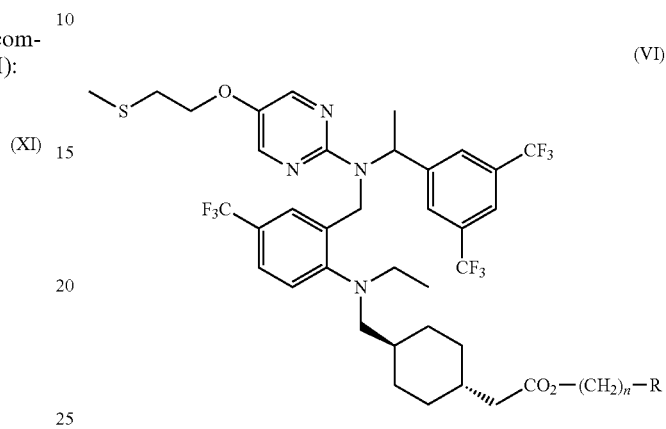

(VI)

(in the formula, R and n have the same meanings as those defined above) with an oxidizing agent in a solvent to prepare the (S)-isomer-dominant semi-chiral compound of a compound represented by the general formula (IV).

12. A medicament comprising the compound, or a salt thereof, or a solvate thereof according to claim 3 as an active ingredient.

* * * * *

UNITED STATES PATENT AND TRADEMARK OFFICE
CERTIFICATE OF CORRECTION

PATENT NO. : 8,906,895 B2
APPLICATION NO. : 13/700849
DATED : December 9, 2014
INVENTOR(S) : T. Ohgiya et al.

It is certified that error appears in the above-identified patent and that said Letters Patent is hereby corrected as shown below:

In the claims

Column 52, lines 58-62 (claim 4, lines 1-5) of the printed patent, "(S)-trans-{4-[({2-[({1-[3,5bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic" should read --(S)-trans-{4-[({2-[({1-[3,5-bis(trifluoromethyl)phenyl]ethyl}{5-[2-(methylsulfonyl)ethoxy]pyrimidin-2-yl}amino)methyl]-4-(trifluoromethyl)phenyl}(ethyl)amino)methyl]cyclohexyl}acetic--

Signed and Sealed this
Thirteenth Day of October, 2015

Michelle K. Lee
*Director of the United States Patent and Trademark Office*

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggtgttcaag gagcatgcaa ag                                              22

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgacaagatg tcctgctgcc a                                               21
```